(12) United States Patent
Alanine et al.

(10) Patent No.: US 6,831,087 B2
(45) Date of Patent: Dec. 14, 2004

(54) PYRIDINE SUBSTITUTED ISOQUINOLINE DERIVATIVES

(75) Inventors: Alexander Alanine, Schlierbach (FR); Bernd Buettelmann, Schopfheim (DE); Marie-Paule Heitz Neidhart, Hagenthal le Bas (FR); Emmanuel Pinard, Linsdorf (FR); Rene Wyler, Zuerich (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/282,365

(22) Filed: Oct. 29, 2002

(65) Prior Publication Data

US 2003/0119870 A1 Jun. 26, 2003

(30) Foreign Application Priority Data

Nov. 9, 2001 (EP) .............................. 01126467

(51) Int. Cl.$^7$ ...................... C07D 401/02; A61K 31/47
(52) U.S. Cl. ........................ 514/307; 546/144
(58) Field of Search ................. 514/307, 314; 546/144, 167

(56) References Cited

FOREIGN PATENT DOCUMENTS

| EP | 1088818 | 4/2001 |
|---|---|---|
| EP | 1090917 | 4/2001 |
| WO | WO 97/23458 | 7/1997 |

OTHER PUBLICATIONS

Chatani, Journal of the American Chemical Society, vol. 122, No. 51, pp. 12882–12883, 2000.*
E. Saxena et al., *Indian J. Chem*, vol. 19 B, pp. 873–878 (*1980*).
N. Chatani et al., *J. Am. Chem. Soc.*, vol. 123, pp. 10935–10941 (*2001*).
Davies & Shipton, *J. Chem. Soc. Perkins Trans. 1*, pp. 501–507 (*1991*).
S. Zimmerman et al., *J. Am. Chem. Soc.*, vol. 113, p. 183–196 (1991).

* cited by examiner

Primary Examiner—Zinna Northington Davis
(74) Attorney, Agent, or Firm—George W. Johnston; Patricia S. Rocha-Tramaloni; Kimberly J. Prior

(57) ABSTRACT

The invention relates to compounds of formulae:

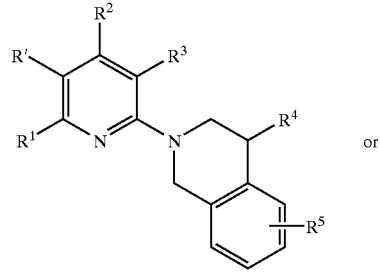

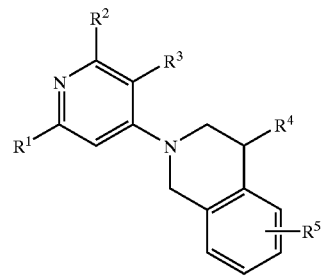

Compounds of the invention have a good affinity to the NMDA receptor and are useful for the treatment of diseases related to this receptor.

23 Claims, No Drawings

PYRIDINE SUBSTITUTED ISOQUINOLINE DERIVATIVES

BACKGROUND

The present invention relates to compounds of formula:

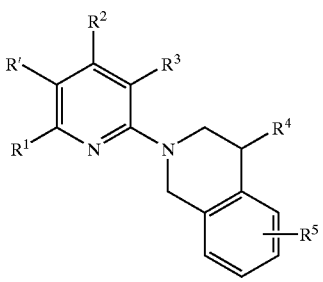

IA or

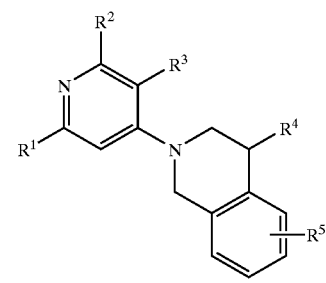

IB

Compounds of the present invention are NMDA(N-methyl-D-aspartate)-receptor subtype selective blockers.

Under pathological conditions of acute and chronic forms of neurodegeneration overactivation of NMDA receptors is a key event for triggering neuronal cell death. NMDA receptors are composed of members from two subunit families, namely NR-1 (8 different splice variants) and NR-2 (A to D) originating from different genes. Members from the two subunit families show a distinct distribution in different brain areas. Heteromeric combinations of NR-1 members with different NR-2 subunits result in NMDA receptors displaying different pharmaceutical properties. Possible therapeutic indications for NMDA NR-2B receptor subtype specific blockers include acute forms of neurodegeneration caused, e.g., by stroke and brain trauma, and chronic forms of neurodegeneration such as Alzheimer's disease, Parkinson's disease, Huntington's disease, ALS (amyotrophic lateral sclerosis), neurodegeneration associated with bacterial or viral infections, and, in addition, depression and chronic and acute pain.

SUMMARY

A compound of formulae:

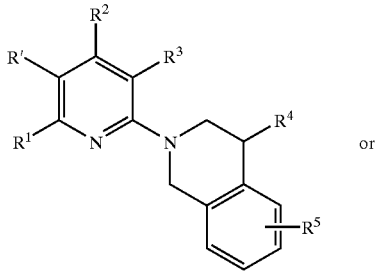

I-A or

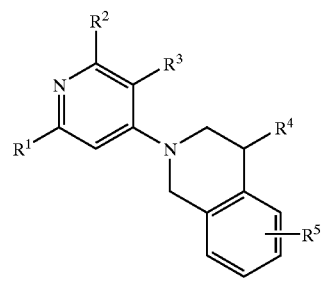

I-B wherein $R^1$ and $R^2$ are independently selected from the group consisting of hydrogen, lower alkyl, —$(CH_2)_n$—OH, —$(CH_2)_n$—$N(R^6)_2$, —$NR^6C(O)C(O)O$-lower alkyl, —$NR^6$—$(CH_2)_n$—OH, —$NR^6C(O)$-lower alkyl, —NH-benzyl and $NR^6C(O)$—$(CH_2)_n$—OH;
$R^6$ is independently hydrogen or lower alkyl;
R' is hydrogen or lower alkyl;
$R^3$ is hydrogen or amino;
$R^4$ is hydrogen or lower alkyl;
$R^5$ is hydrogen or halogen; or
$R^1$ and R' together with the carbon atoms to which they are attached form the group —$(CH_2)_4$—; or
$R^2$ and $R^3$ together with the carbon atoms to which they are attached form the group —$N(R^6)$—$CH_2$—O—$CH_2$—; and
n is 0, 1, 2 or 3;
or a pharmaceutically acceptable acid addition salt thereof.

The compounds of formula IA and IB and their salts are distinguished by valuable therapeutic properties. Compounds of the present invention are NMDA(N-methyl-D-aspartate)-receptor subtype selective blockers, which have a key function in modulating neuronal activity and plasticity. Accordingly, compounds of the invention are useful in mediating processes underlying development of CNS as well as learning and memory formation.

The present invention relates to compounds of formula IA, IB, combinations thereof and pharmaceutically acceptable acid addition salts thereof, and the preparation of the compounds of formula IA, IB and salts thereof. The present invention also relates to pharmacuetical compositions containing a compound of formula IA, IB, combinations thereof or a pharmaceutically acceptable acid addition salt thereof and the preparation of such pharmaceutical compositions.

The invention also relates to a method of treatment of diseases responsive to modulation of NMDA(N-methyl-D-aspartate)-receptors by subtype selective blockers, comprising administering a therapeutically effective amount of the compounds of formula IA, IB, combinations thereof or their pharmaceutically acceptable salts to a patient in need of such treatment.

DETAILED DESCRIPTION

The following definitions of the general terms used in the present description apply irrespective of whether the terms in question appear alone or in combination.

As used herein, the term "lower alkyl" denotes a straight- or branched-chain alkyl group containing from 1 to 7 carbon atoms, for example, methyl, ethyl, propyl, isopropyl, butyl and the like. Preferred lower alkyl groups contain from 1 to 4 carbon atoms.

The term "halogen" denotes chlorine, iodine, fluorine and bromine.

The term "pharmaceutically acceptable acid addition salts" embraces salts with inorganic and organic acids, such as hydrochloric acid, nitric acid, sulfuric acid) phosphoric acid, citric acid, formic acid, fumaric acid, maleic acid, acetic acid, succinic acid, tartaric acid, methane-sulfonic acid, p-toluenesulfonic acid and the like.

Compounds of formula IA are preferred.

Exemplarly preferred compounds of formula IA, are those wherein $R^2$ is amino, selected from the group consisting of 2-(3,4-dihydro-1H-isoquinolin-2-yl)-pyridin-4-yl-amine, Rac.-2-(4-methyl-3,4-dihydro-1H-isoquinolin-2-yl)-pyridin-4-yl-amine, 2-(3,4-dihydro-1H-isoquinolin-2-yl)-5-methyl-pyridin-4-yl-amine, 2-(3,4-dihydro-1H-isoquinolin-2-yl)-1-methyl-pyridin-4-yl-amine, 2-(3,4-dihydro-1H-isoquinolin-2-yl)-6-methyl-pyridin-4-yl-amine and

[4-amino-6-(3,4-dihydro-1H-isoquinolin-2-yl)-pyridin-2-yl]-methanol

Other preferred compounds of formula IA are those, wherein $R^2$ is —NH(CH$_2$)$_2$OH. Examples of these preferred compounds are selected from the group consiting of 2-[2-(3,4-dihydro-1H-isoquinolin-2-yl)-pyridin-4-yl-amino]-ethanol, 2-[2-(3,4-dihydro-1H-isoquinolin-2-yl)-6-methyl-pyridin-4-yl-amino]-ethanol and 2-[2-(3,4-dihydro-1H-isoquinolin-2-yl)-5-methyl-pyridin-4-yl-amino]-ethanol.

Compounds of formula IA, wherein $R^2$ is —NH-lower alkyl, are also preferred, for example compounds selected from the group consisting of:

[2-(3,4-dihydro-1H-isoquinolin-2-yl)-pyridin-4-yl]-methyl-amine and

[2-(3,4-dihydro-1H-isoquinolin-2-yl)-pyridin-4-yl]-dimethyl-amine.

Compounds of formula IB are also preferred.

Preferred compounds of formula IB, wherein $R^2$ is hydrogen, are selected from the group consisting, of 2-pyridin-4-yl-1,2,3,4-tetrahydro-isoquinoline and 2-(2-methyl-pyridin-4-yl)-1,2,3,4-tetrahydro-isoquinoline.

Further preferred compounds of formula IB are those, wherein $R^2$ is amino, for example selected from the group consisting of:

4-(3,4-dihydro-1H-isoquinolin-2-yl)-pyridin-2-yl-amine or 4-(3,4-dihydro-1H-isoquinolin-2-yl)-6-methyl-pyridin-2-yl-amine.

Compounds of formula IB, wherein $R^2$ is —NHC(O)C(O)OCH$_2$CH$_3$ or —NH(CH$_2$)$_2$OH are also preferred and selected from the group consisting of N-[4-(3,4-dihydro-1H-isoquinolin-2-yl)-6-methyl-pyridin-2-yl]-oxalamic acid ethyl ester and 2-[4-(3,4-dihydro-1H-isoquinolin-2-yl)-6-methyl-pyridin-2-yl-amino]-ethanol The compounds of formulae IA and IB can be prepared in accordance with the invention by reacting a compound of formula:

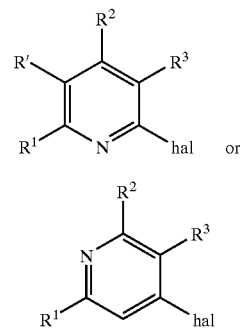

IIA or

IIB with a compound of formula:

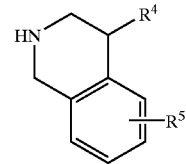

III forming a compound of formula:

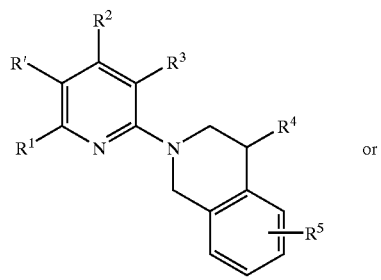

IA or

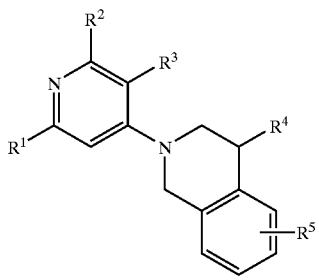

IB wherein $R^1$–$R^5$ and R' have the significances given above and hal is bromo or chloro, or reacting a compound of formula:

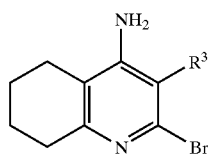

IIA3 with a compound of formula:

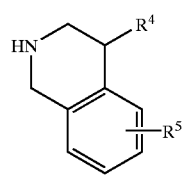

III forming a compound of formula:

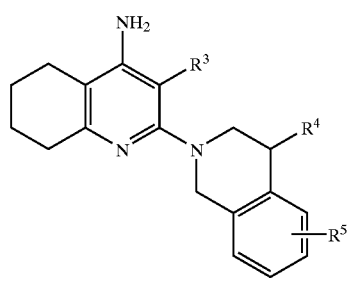

IA1 wherein $R^3$–$R^5$ have the significances given above, or reacting a compound of formula:

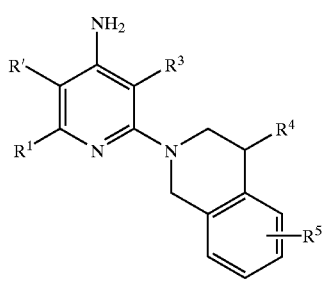

IA2 or

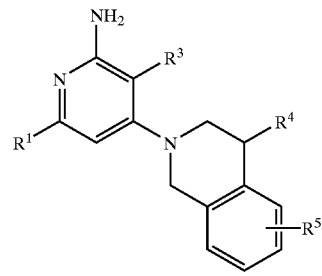

IB2 with $ClC(O)C(O)OCH_2CH_3$
forming a compound of formula:

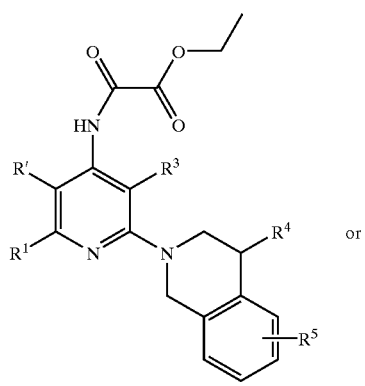

IA3 or

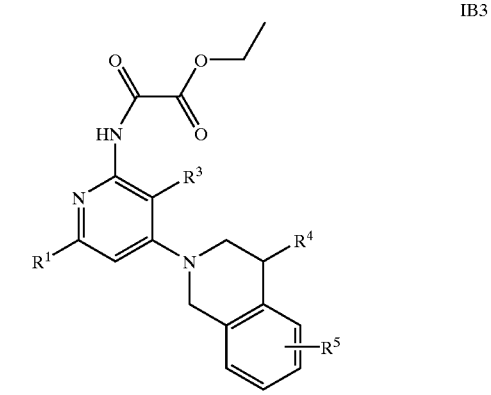

IB3 wherein $R^1$, $R^3$–$R^5$ and R' have the significances given above, or reducing a compound of formula:

IA3

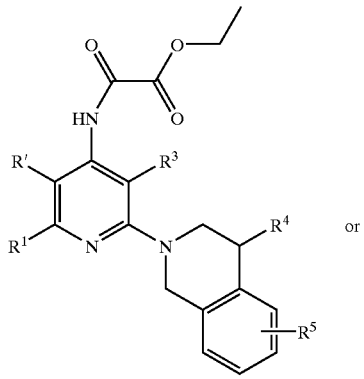

or

IB3

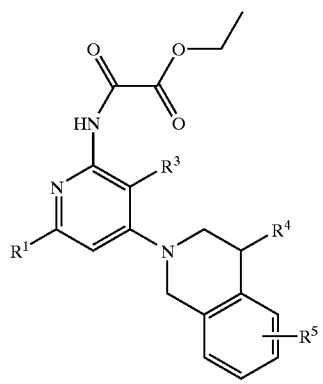

with an reducing agent, such as AlLiH$_4$/THF thereby forming a compound of formula:

IA4

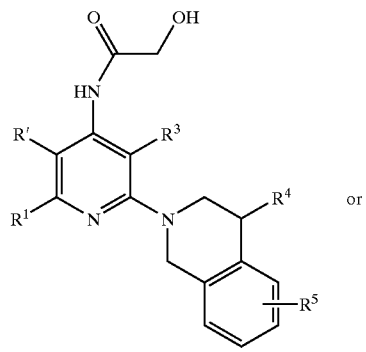

or

IB4

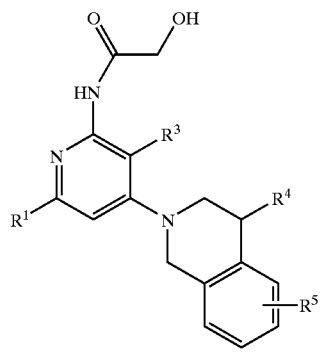

or further reducing compounds IA4 or IB4 to a compound of formula:

IA5

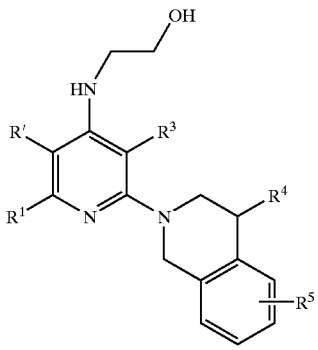

or

IB5

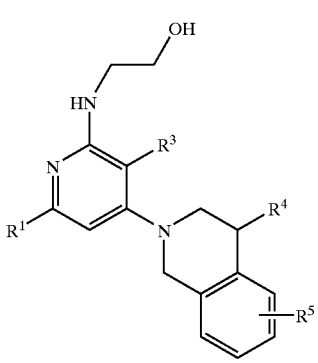

wherein R$^1$, R$^3$–R$^5$ and R' have the significances given above, or reacting a compound of formula:

IA2

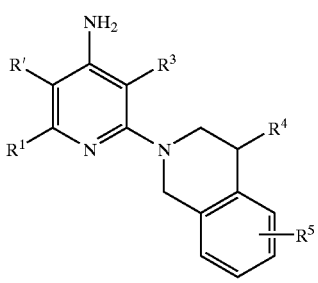

or

IB2

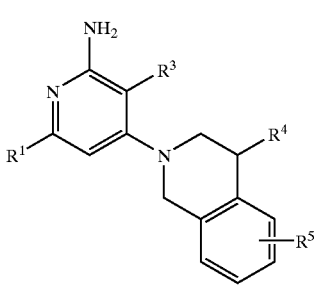

with ClC(O)OCH$_2$CH$_3$ or with CH$_3$C(O)Cl or with ClC(O)-phenyl or with CHOOH/CH$_2$O, respectively forming a compound of formula:
IA6
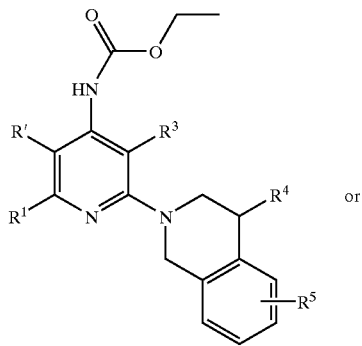
or
IB6
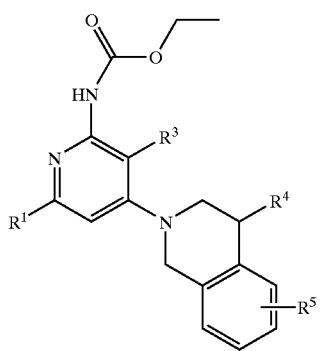
or of formula:
IA7
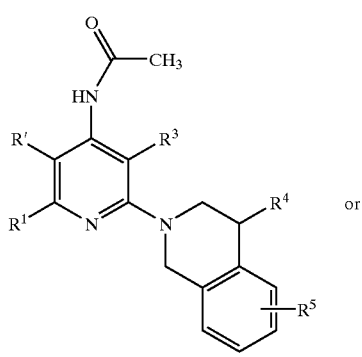
or
IB7
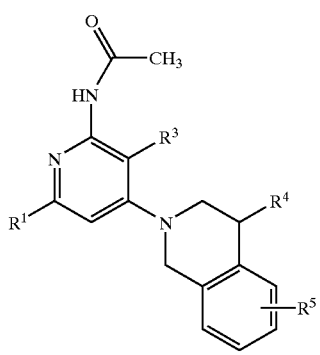
or of formula:
IA8
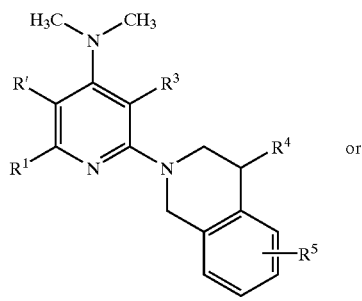
or
IB8
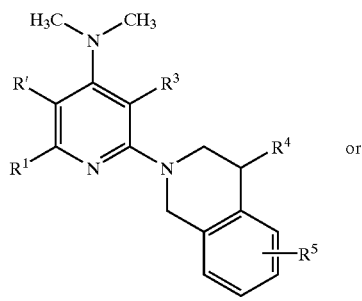
or of formula:
IA9
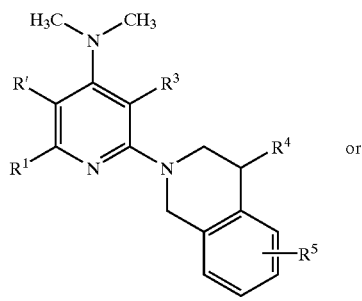
or
IB9
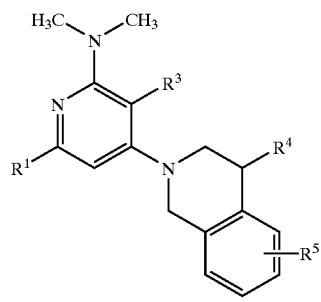
wherein $R^1$, $R^3$–$R^5$ and R' have the significances given above, or reacting a compound of formulae:

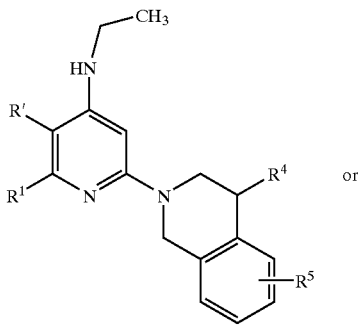

IA10

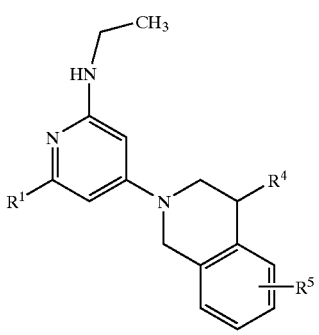

IB10 with HCOOH/CH$_2$O
to give a compound of formulae:

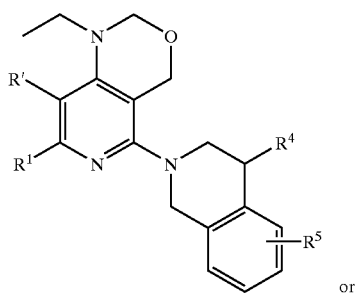

IA11 or

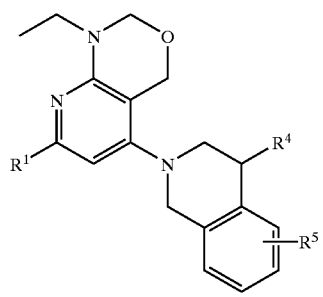

IB11 wherein R$^1$, R$^4$, R$^5$ and R' have the significances given above, and if desired, converting the compound of formula I obtained into a pharmaceutically acceptable salt.

In the following the preparation of compounds of formula IA and IB are described in more detail:

In accordance with the process variants, described above, and with schemes 1–12, described below, compounds of formula IA and IB may be prepared by known procedures, for example by the followings:

A mixture of a compound of formula IIA or IIB, for example 2-bromo-pyridin-4-yl-amine or 4-bromo-pyridin-2-yl-amine, respectively, and a compound of formula III, such as 1,2,3,4-tetrahydro-isoquinoline is stirred at 150° C. for about 3 hr. After extractive workup the organic phase is dried and concentrated to give the free base of a compound of general formulae IA or IB.

Compounds of formula IIA1 may be prepared as follow:

To a solution of a compound of formula IIA, for example 2-bromo-6-ethyl-pyridine (S. G. Davies and M. R. Shipton, J. Chem. Soc., Perkin Trans. 1, 1991, 3, 501) in acetic acid is added peracetic acid, maintaining T<50° C. After complete addition the mixture is stirred at about 50° C. for 5 hr and then cooled to rt. Crushed ice is added and the pH is adjusted to pH 12 with aqueous KOH solution. After extraction the combined organic phases are dried and evaporated to give the corresponding oxide of formula IVA. Then, with ice bath cooling HNO$_3$ is added dropwise, followed by H$_2$SO$_4$. The mixture is stirred at about 90° C. for 90 min and then cooled to rt. Crushed ice is added and the pH is adjusted to pH 12 with aqueous NaOH solution. After extraction the combined organic phases are dried and evaporated to give a compound of formula VA, wich is directly used in the next step. A solution of a compound of formula VA in acetic acid is treated with powdered iron. The mixture is slowly heated to 100° C. and kept for 1 hr at this temperature. Then the reaction mixture is cooled to rt and filtered. After evaporation of the solvent the residue is crystallized to yield a compound of formula IIA1.

The corresponding compounds of formula IA may be prepared as described above.

Furthermore, compounds of formula IIA2 may be prepared as follows:

To a solution of a compound of formula VA1, for example 2-bromo-6-methyl-4-nitro-pyridine (A. Puszko, Pr. Nauk. Akad. Ekon. im. Oskara Langego Wroclawiu, 1984, 278, 169) in conc. H$_2$SO$_4$, CrO$_3$ is added maintaining T<55° C. After about 4 hr the mixture is heated to 70° C. for 30 min and then cooled to rt. Ice-cold water is added maintaining T<70° C. The mixture is left overnight. A compound of formula VA2 is obtained. A corresponding solution of these compounds in THF is treated with borane/THF. The mixture is refluxed for 6 hr, then powdered iron is added, followed by acetic acid. Reflux is maintained for 6 hr, the mixture is filtered, evaporated, partitioned, dried and concentrated to give a compound of formula IIA2. The corresponding compounds of formulae IA may then be prepared as described above.

A compound of formula IIA3 maybe prepared in the following way: With efficient ice bath cooling a compound of formula VI, for example 2-bromo-5,6,7,8-tetrahydro-quinoline 1-oxide (S. Zimmermann et al., J. Am. Chem. Soc., 1991, 113, 183) is treated with conc. H$_2$SO$_4$, followed by conc. HNO$_3$. The resulting mixture is heated to about 90° C. for 90 min, cooled and poured on crushed ice. NaOH is added to reach pH 7 and the aqueous phase is extracted, dried and concentrated to yield a compound of formula VII.

A mixture of a compound of formula VII, for example 2-bromo-4-nitro-5,6,7,8-tetrahydro-quinoline 1-oxide, powdered iron and acetic acid is heated to about 100° C. for 1 hr. After cooling the mixture is filtered, evaporated and the residue is partitioned. The organic phase is dried and concentrated to provide a compound of formula IIA3. The corresponding compounds of formulae IA1 may then be prepared as described above.

Furthermore, a compound of formulae IA3 or IB3 may be prepared by reaction of a compound of formula IA2 or IB2, with ethyl chlorooxoacetate. The obtained compound of formula IA3 or IB3 is then reacted with lithium aluminum hydride. After workup and chromatography the free base of a compound of formulae IA4 and IA5 or IB4 and IB5 may be obtained.

Compounds of formula IA9 or IB9 may be prepared as follows:

A solution of a compound of formula IA2 or IB2, for example 2-(3,4-dihydro-1H-isoquinolin-2-yl)-pyridin-4-yl-amine in formic acid is treated with aqueous formaldehyde solution. The mixture is refluxed for 1 hr followed by evaporation of the volatiles. The residue is partitioned and the organic phase is separated, dried and concentrated.

Compounds of formulae IA6, IB6, IA7, IB7, IA8 or IB8 may be obtained from a compound of formula IA2 or IB2 with ethyl chloroformate, acetylchloride or benzoyl chloride, respectively. These reactions are carried out in conventional manner.

In accordance with schemes 11 and 12, a compound of formula IA11 or IB11 or similar compounds maybe prepared from a solution of a compound of formula IA10 or IB10, for example [2-(3,4-dihydro-1H-isoquinolin-2-yl)-pyridin-4-yl]-ethyl-amine, in formic acid This solution is treated with aqueous formaldehyde solution. The mixture is refluxed for 1 hr followed by evaporation of the volatiles. The residue is partitioned and the organic phase is separated, dried and concentrated to obtain a compound of formula IA11 or IB11.

Pharmaceutically acceptable salts can be manufactured according to methods which are known in the art. The acid addition salts of compounds of formula IA and IB are especially well suited for pharmaceutical use.

In the following schemes 1–12 are described processes for preparation of compounds of formula I, starting from known compounds, from commercial products or from compounds, which can be prepared in conventional manner.

The preparation of compounds of formulae IA and IB are described in more detail in working examples 1–35

Scheme 1

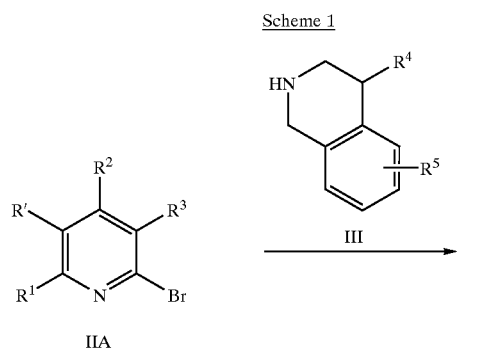

The substituents $R^1$ to $R^5$ and R' are described above.

Scheme 2

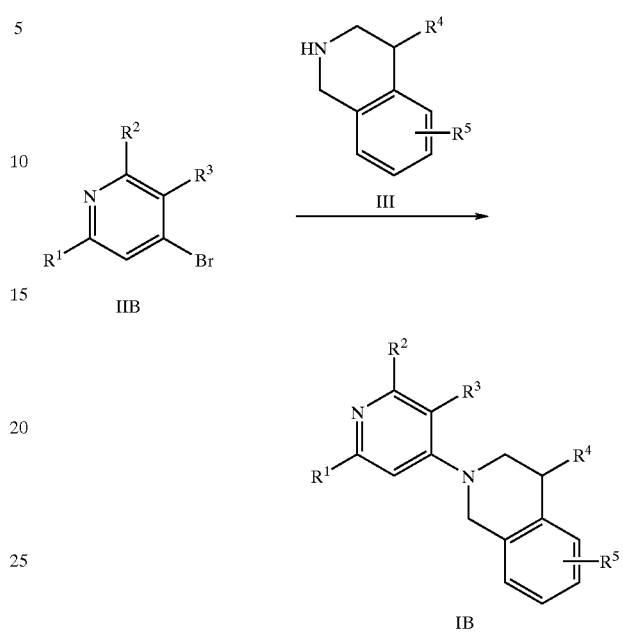

The substituents $R^1$ to $R^5$ and R' are described above.

Scheme 3

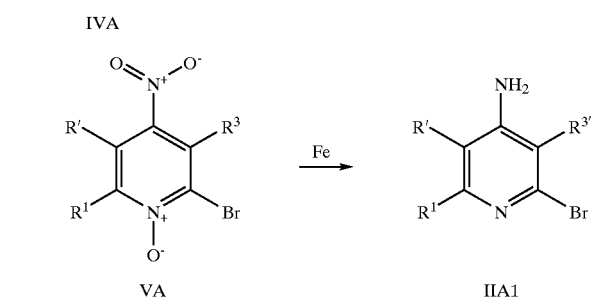

The substituents $R^1$, $R^3$ and R' are described above.

Scheme 4

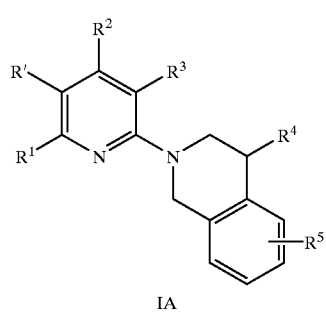

The substituents $R^1$ and $R^3$ are described above.
wherein $R^3$–$R^5$ have the significances given above.
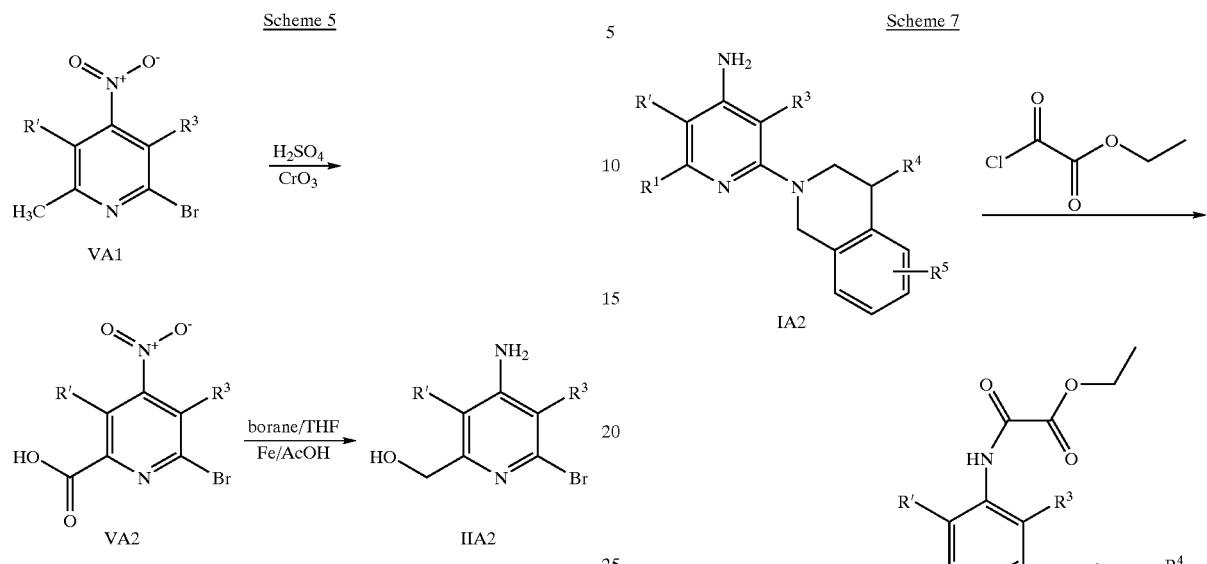
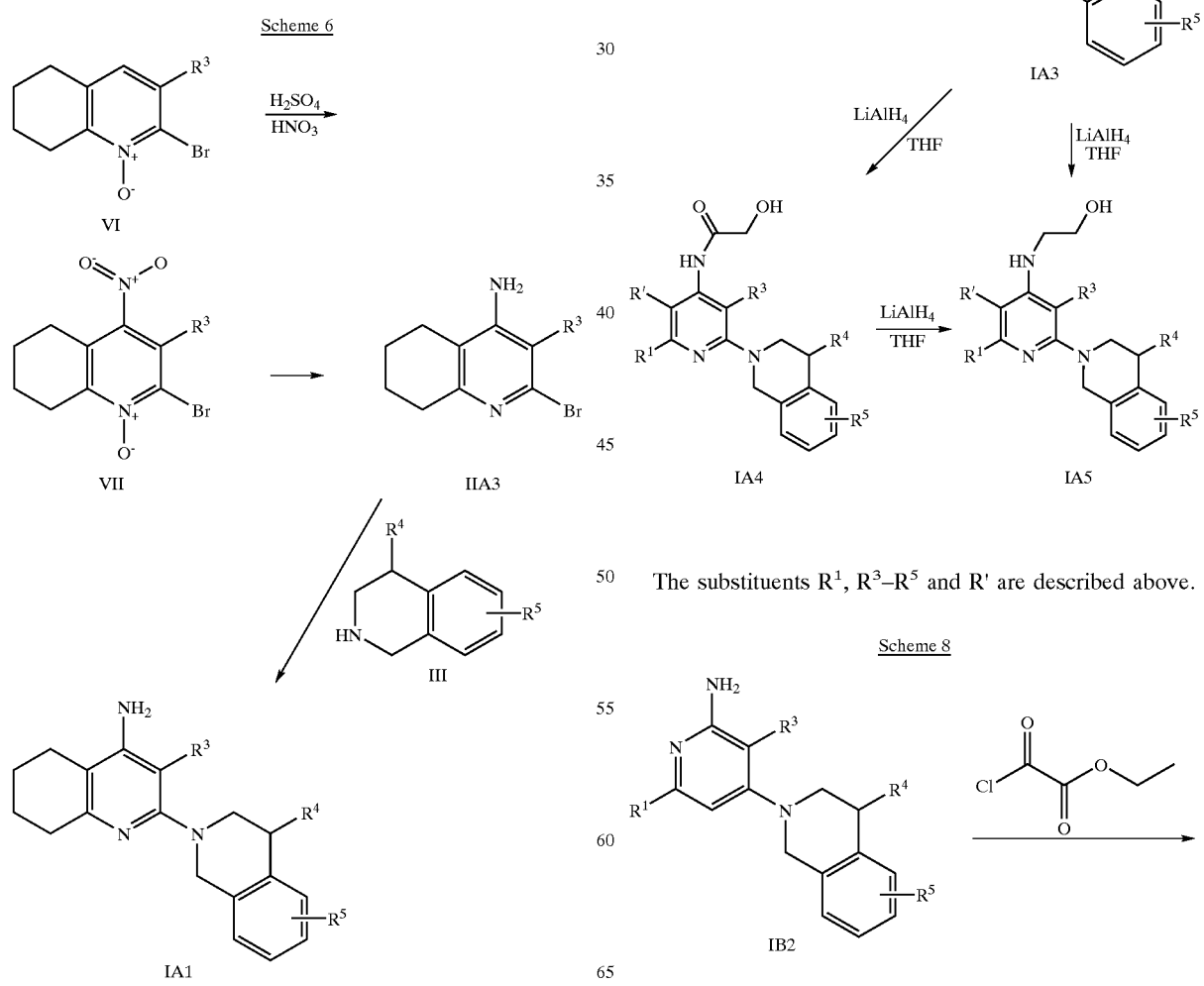
The substituents R' and $R^3$ are described above.
The substituents $R^1$, $R^3$–$R^5$ and R' are described above.

-continued
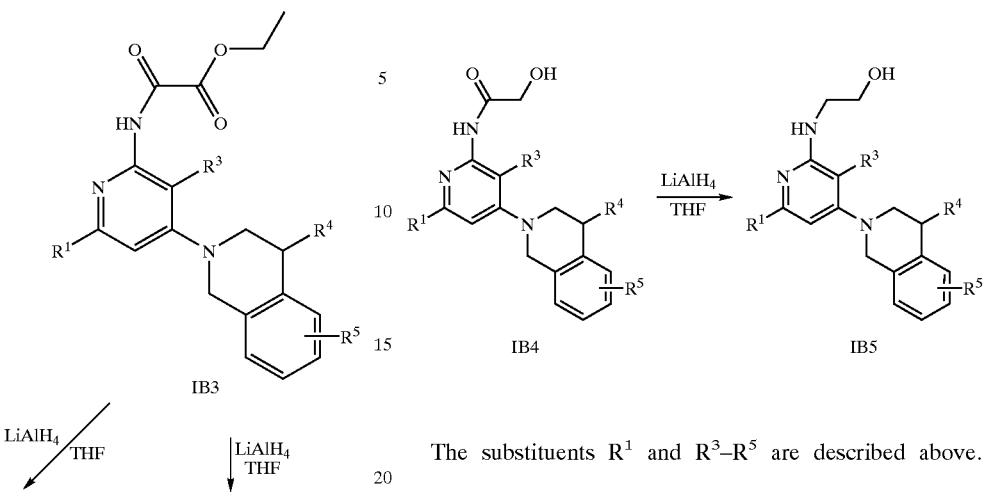
The substituents $R^1$ and $R^3$–$R^5$ are described above.
Scheme 9
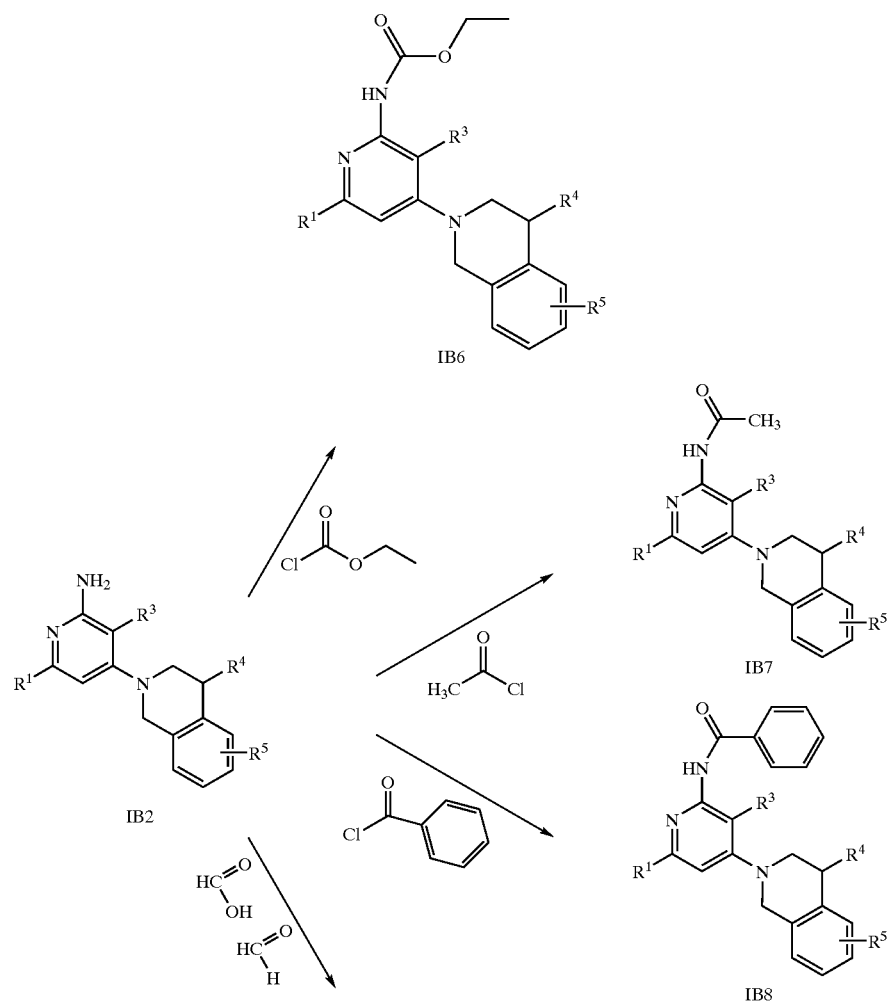

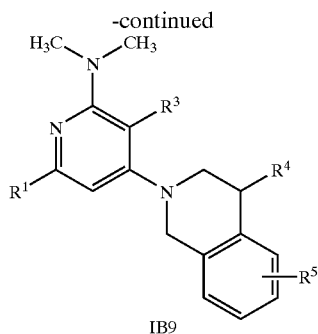
IB9
The substituents $R^1$ and $R^3$–$R^5$ are described above.
Scheme 10
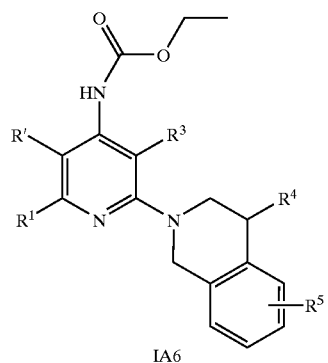
IA6
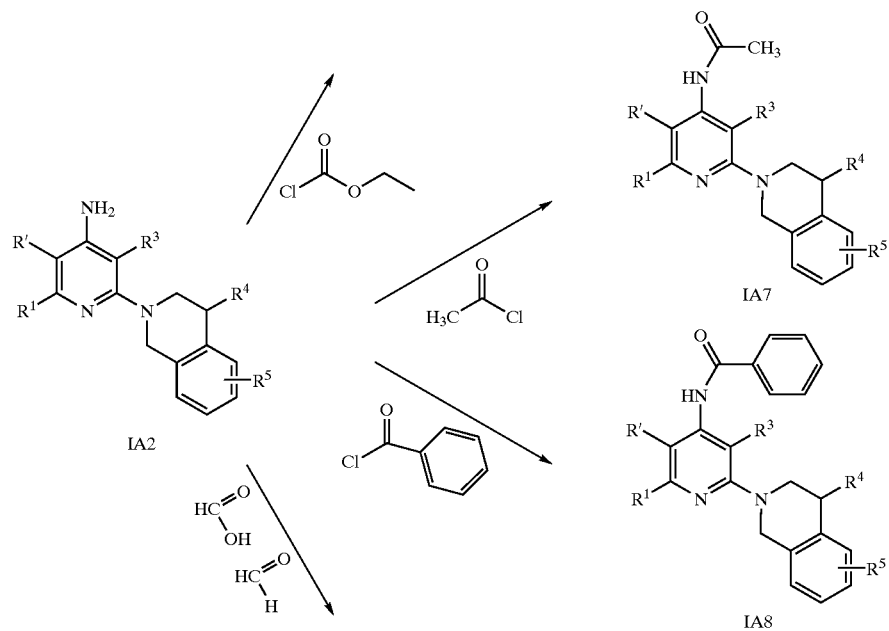

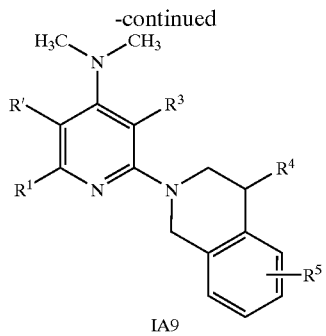

IA9

The substituents $R^1$, $R^3$–$R^5$ and $R'$ have been described above.

Scheme 11

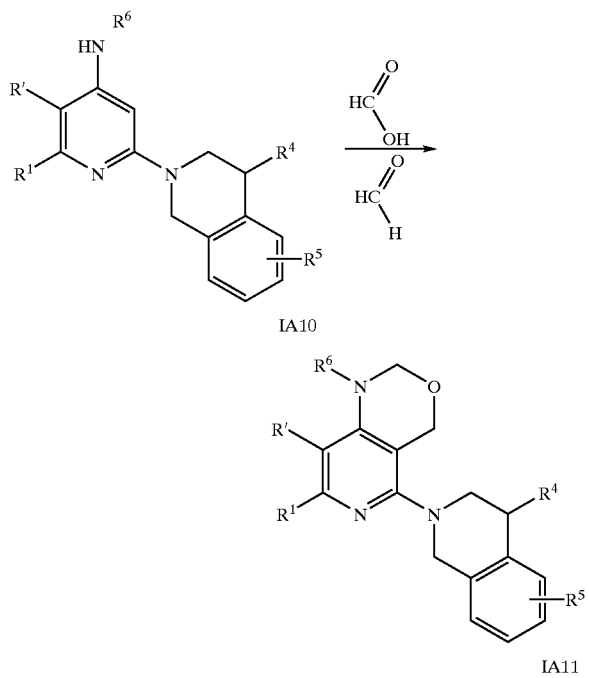

The substituents $R^1$, $R'$, $R^4$, $R^5$ and $R^6$ have been described above.

Scheme 12

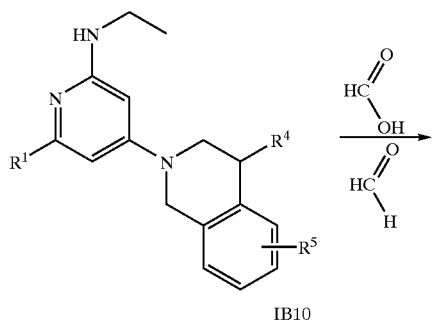

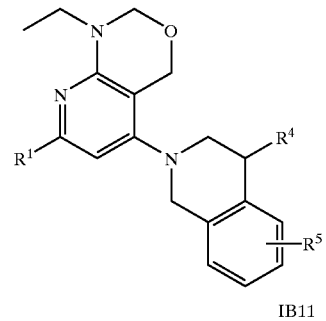

IB11

The substituents $R^1$, $R^4$ and $R^5$ are described above.

As mentioned earlier, the compounds of formulae IA and IB, combinations of IA and IB and their pharmaceutically usable acid addition salts possess valuable pharmacodynamic properties. Compounds of formulae IA and IB are NMDA-receptor subtype 2B selective blockers, which have a key function in modulating neuronal activity and plasticity. Accordingly, compounds of the invention are useful in mediating processes underlying development of CNS as well as learning and memory formation.

The compounds of formulae IA and IB1 were investigated in accordance with the test given hereinafter.

Test Method $^3$H-Ro 25-6981 binding (Ro 25-6981 is [R-(R*,S*)]-α-(4-hydroxy-phenyl)-β-methyl-4-(phenyl-methyl)-1-piperidine propanol)

Male Füllinsdorf albino rats weighing between 150–200 g were used. Membranes were prepared by homogenization of the whole brain minus cerebellum and medulla oblongata with a Polytron (10.000 rpm, 30 seconds), in 25 volumes of a cold Tris-HCl 50 mM, EDTA 10 mM, pH 7.1 buffer. The homogenate was centrifuged at 48,000 g for 10 minutes at 4° C. The pellet was resuspended using the Polytron in the same volume of buffer and the homogenate was incubated at 37° C. for 10 minutes. After centrifugation the pellet was homogenized in the same buffer and frozen at –80° C. for at least 16 hours but not more than 10 days. For the binding assay the homogenate was thawed at 37° C., centrifuged and the pellet was washed three times as above in a Tris-HCl 5 mM, pH 7.4 cold buffer. The final pellet was resuspended in the same buffer and used at a final concentration of 200 mg of protein/ml.

$^3$H-Ro 25-6981 binding experiments were performed using a Tris-HCl 50 mM, pH 7.4 buffer. For displacement experiments 5 nM of $^3$H-Ro 25-6981 were used and non specific binding was measured using 10 mM of tetrahydroisoquinoline and usually it accounts for 10% of the total. The incubation time was 2 hours at 4° C. and the assay was stopped by filtration on Whatmann GF/B glass fiber filters (Unifilter-96, Packard, Zurich, Switzerland). The filters were washed 5 times with cold buffer. The radioactivity on the filter was counted on a Packard Top-count microplate scintillation counter after addition of 40 mL of microscint 40 (Canberra Packard S. A., Zürich, Switzerland).

The above procedure was performed to determine data for calculation of an $IC_{50}$ value. The $IC_{50}$ value is a concentration expressed in micromoles ($\mu$M) for a test compound at which 50% of the ligand (in this determination, $^3$H-Ro 25-6981) bonded to the receptor is displaced. The binding ability of the compounds of the invention was measured in vitro using a minimum of 10 concentrations and repeated at least once. The specific binding at each concentration was then calculated as the % of the maximum specific binding (100%) obtained in the same experiment, in the absence of a test compound. Competitive displacement of $^3$H-Ro 25-6981 was observed, with complete displacement of the radioligand from specific binding sites (usually about 0% of specific binding at the highest concentrations tested). An $IC_{50}$ value was then calculated with all the ten datapoints (% of specific bound) by plotting the data on a semilogarithmic scale with a sigmoidal fit (Log of the molar concentration on X-axis vs. % of specific bound on the Y-axis) using Microsoft Excel fit software or Microcal Origin software. The pooled normalized values were analyzed using a non-linear regression calculation program which provide $IC_{50}$ with their relative upper and lower 95% confidence limits.

The $IC_{50}$ ($\mu$M) of preferred compounds of formulae IA and IB, tested in accordance with the above mentioned methods, is <0.02 $\mu$M. In table I below some $IC_{50}$ values of preferred compounds are shown.

TABLE I

| Example No. | $IC_{50}$ ($\mu$M) |
| --- | --- |
| 1 | 0.008 |
| 3 | 0.011 |
| 4 | 0.014 |
| 5 | 0.0053 |
| 6 | 0.011 |
| 9 | 0.006 |
| 10 | 0.011 |
| 30 | 0.004 |
| 31 | 0.02 |
| 32 | 0.011 |
| 33 | 0.02 |
| 35 | 0.004 |

The compounds of formulae IA and IB, combinations of formulae IA and IB and their salts, as herein described, can be incorporated into standard pharmaceutical dosage forms, for example, for oral or parenteral application with the usual pharmaceutically acceptable adjuvant materials, for example, organic or inorganic inert carrier materials, such as, water, gelatin, lactose, starch, magnesium stearate, talc, vegetable oils, gums, polyalkylene-glycols and the like. The pharmaceutical compositions can be employed in a solid form, for example, as tablets, suppositories, capsules, or in liquid form, for example, as solutions, suspensions or emulsions. Pharmaceutically acceptable adjuvant materials can be added and include preservatives stabilizers, wetting or emulsifying agents, salts to change the osmotic pressure or to act as buffers. The pharmaceutical compositions can also contain other therapeutically active substances.

The dosage can vary within wide limits and will, of course, be fitted to the individual requirements in each particular case. In the case of oral administration the dosage lies in the range of about 0.1 mg per dosage to about 1000 mg per day of a compound of (general formula I although the upper limit can also be exceeded when this is shown to be indicated.

The following examples illustrate the present invention in more detail. However, they are not intended to limit its scope in any manner. All temperatures are given in degree Celsius.

EXAMPLE 1

2-(3,4-Dihydro-1H-isoquinolin-2-yl)-pyridin-4-yl-amine 1:1 hydrochloride

A mixture of 2-bromo-pyridin-4-yl-amine (0.50 g, 2.9 mmol) and 1,2,3,4-tetrahydro-isoquinoline (1.1 g, 8.7 mmol) was stirred at 150° C. for 3 hr. After extractive workup (AcOEt/H$_2$O) the organic phase was dried (Na$_2$SO$_4$), concentrated and chromatographed (SiO$_2$ with CH$_2$Cl$_2$/CH$_3$OH/NH$_4$OH=140/10/1) to give the free base of the title compound (0.39 g, 60%) as a colorless oil. Treatment with hydrogen chloride gave white crystals. Mp. 252° C. (dec.) (isopropanol/AcOEt), MS: m/e=226 (M+H$^+$).

EXAMPLE 2

Rac.-2-(4-Methyl-3,4-dihydro-1H-isoquinolin-2-yl)-pyridin-4-yl-amine 1:1 fumarate Following the general method described in example 1, the title compound was obtained as a white crystalline material by reaction of 2-bromo-pyridin-4-yl-amine with rac.-4-methyl-1,2,3,4-tetrahydro-isoquinoline (G. Grunewald et al., J. Med. Chem., 1988, 31, 433) and crystallization of the free base as the fumarate salt. Mp. 178–179° C. (MeOH/Et$_2$O), MS: m/e=239 (M$^+$).

EXAMPLE 3

2-(3,4-Dihydro-1H-isoquinolin-2-yl)-5-methyl-pyridin-4-yl-amine 1:1 fumarate

Following the general method described in example 1, the title compound was obtained as a white crystalline material by reaction of 2-bromo-5-methyl-pyridin-4-yl-amine (A. Puszko, Z. Talik, Pr. Nauk. Akad. Ekon. im. Oskara Langego Wroclawiu, 1980, 167, 177) with 1,2,3,4-tetrahydro-isoquinoline and crystallization of the free base as the fumarate salt. Mp. 110° C. (dec.) (MeOH/Et$_2$O), MS: m/e=240 (M+H$^+$).

EXAMPLE 4

2-(3,4-Dihydro-1H-isoquinolin-2-yl)-6-methyl-pyridin-4-yl-amine 1:1 fumarate

Following the general method described in example 1, the title compound was obtained as a white crystalline material by reaction of 2-bromo-6-methyl-pyridin-4-yl-amine (A. Puszko, Pr. Nauk. Akad. Ekon. im. Oskara Langego Wroclawiu, 1984, 278, 169) with 1,2,3,4-tetrahydro-isoquinoline and crystallization of the free base as the fumarate salt. Mp. 110° C. (dec.) (MeOH/Et$_2$O), MS: m/e=239 (M$^+$).

EXAMPLE 5

2-(3,4-Dihydro-1H-isoquinolin-2-yl)-6-ethyl-pyridin-4-yl-amine 1:1 fumarate b) 2-Bromo-6-ethyl-pyridine 1-oxide To a solution of 2-bromo-6-ethyl-pyridine (15.4 g, 82.8 mmol) (S. G. Davies and M. R. Shipton, J. Chem. Soc., Perkin Trans. 1, 1991, 3, 501) in acetic acid (15 ml) was added peracetic acid (26 ml of a 39% solution) maintaining T<50° C. After complete addition the mixture was stirred at 50° C. for 5 hr and then cooled to room temperature (rt). Crushed ice (40 g) was added and the pH was adjusted to pH 12 with 40% aqueous KOH solution. After extraction with CHCl₃ (6×60 ml) the combined organic phases were dried (Na₂CO₃) and evaporated to give 20.0 g (>100%) of the title compound, MS: m/e=201 (M⁺) as a yellow oil.

b) 2-Bromo-6-ethyl-4-nitro-pyridine 1-oxide

With ice bath cooling HNO₃ (100%, 25 ml) was added dropwise to 2-bromo-6-ethyl-pyridine 1-oxide (example 5a) (20.0 g, 99 mmol), followed by H₂SO₄ (98%, 17 ml). The mixture was stirred at 90° C. for 90 min and then cooled to rt. Crushed ice (500 g) was added and the pH was adjusted to pH 12 with 28% aqueous NaOH solution. After extraction with AcOEt (4×250 ml) the combined organic phases were dried (Na₂CO₃) and evaporated to give 15.9 g (65%) of a yellow solid mass which was directly used in the next step c) 2-Bromo-6-ethyl-pyridin-4-ylamine A solution of 2-bromo-6-ethyl-4-nitro-pyridine 1-oxide (example 5b) (15.9 g, 69 mmol) in acetic acid (310 ml) was treated with powdered iron (25.8 g, 462 mmol). The mixture was slowly heated to 100° C. and kept for 1 hr at this temperature. Then the reaction mixture was cooled to rt and filtered. After evaporation of the solvent the residue was crystallized to yield the title compound as a beige material (88%). Mp. 75–77° C. (pentane), MS: m/e=200 (M⁺).

d) 2-(3,4-Dihydro-1H-isoquinolin-2-yl)-6-ethyl-pyridin-4-yl-amine 1:1 fumarate

Following the general method described in example 1, the title compound was obtained as a white crystalline material by reaction of 2-bromo-6-ethyl-pyridin-4-yl-amine (example 5c) with 1,2,3,4-tetrahydro-isoquinoline and crystallization of the free base as the fumarate salt. Mp. 140–141° C. (AcOEt), MS: m/e=254 (M+H⁺).

EXAMPLE 6

[4-Amino-6-(3,4-dihydro-1H-isoquinolin-2-yl)-pyridin-2-yl]-methanol a) 6-Bromo-4-nitro-pyridine-2-carboxylic acid To a solution of 2-bromo-6-methyl-4-nitro-pyridine (17.8 g, 82.0 mmol) (A. Puszko, Pr. Nauk. Akad. Ekon. im. Oskara Langego Wroclawiu, 1984, 278) 169) in conc. H₂SO₄ (100 ml) CrO₃ (32.8 g, 328 mmol) was added maintaining T<55° C. After 4 hr the mixture was heated to 70° C. for 30 min and then cooled to rt. Ice-cold water (500 ml) was added maintaining T<70° C. The mixture was left overnight. The title compound crystallized as a beige material (76%). Mp. 173–175° C. (H₂O), MS: m/e=246 (M⁺).

b) (4-Amino-6-bromo-pyridin-2-yl)-methanol

A solution of 6-bromo-4-nitro-pyridine-2-carboxylic acid (example 6a) (6.60 g, 29.1 mmol) in THF (150 ml) was treated with borane/THF (87 ml of a 1M solution). The mixture was refluxed for 6 hr, then powdered iron (16.3 g, 291 mmol) was added, followed by acetic acid (150 ml). Reflux was maintained for 6 hr, the mixture was filtered, evaporated and partitioned (AcOEt/NaHCO₃-solution). The organic phase was dried (Na₂SO₄), concentrated and chromatographed (SiO₂ with CH₂Cl₂/MeOH=93/7) to provide 2.0 g (34%) of (4-amino-6-bromo-pyridin-2-yl)-methanol as a white solid material. Mp. 144–145° C. (AcOEt), MS: m/e=202 (M⁺).

c) [4-Amino-6-(3,4-dihydro-1H-isoquinolin-2-yl)-pyridin-2-yl]-methanol

Following the general method described in example 1, the title compound was obtained as an off-white crystalline material by reaction of (4-amino-6-bromo-pyridin-2-yl)-methanol (example 6b) with 1,2,3,4-tetrahydro-isoquinoline. Mp. 183–184° C. (AcOEt), MS: m/e=255 (M⁺).

EXAMPLE 7

2-(3,4-Dihydro-1H-isoquinolin-2-yl)-5,6,7,8-tetrahydro-quinolin-4-yl-amine 1:1 hydrochloride a) 2-Bromo-4-nitro-5,6,7,8-tetrahydro-quinoline 1-oxide With efficient ice bath cooling 2-bromo-5,6,7,8-tetrahydro-quinoline 1-oxide (8.0 g, 35 mmol) (S. Zimmermann et al., J. Am. Chem. Soc., 1991, 113, 183) was treated with conc. H₂SO₄ (65 ml), followed by conc. HNO₃ (10 ml). The resulting mixture was heated to 90° C. for 90 min, cooled and poured on crushed ice (200 g). NaOH (28%) was added to reach pH 7 and the aqueous phase extracted with AcOEt. The organic phase was dried (Na₂SO₄) and concentrated to yield 7.9 g (83%) of the title compound as a yellow oil. MS: m/e=272 (M⁺).

b) 2-Bromo-5,6,7,8-tetrahydro-quinolin-4-yl-amine

A mixture of 2-bromo-4-nitro-5,6,7,8-tetrahydro-quinoline 1-oxide (example 7a) (7.9 g, 28.9 mmol), powdered iron (13.3 g, 238 mmol) and acetic acid (160 ml) was heated to 100° C. for 1 hr. After cooling the mixture was filtered and evaporated and the residue was partitioned (AcOEt/NaHCO₃-solution). The organic phase was dried (Na₂SO₄), concentrated and chromatographed (SiO₂ with CH₂Cl₂/MeOH=98/2) to provide 2.4 g (37%) of the title compound as a brown solid material. MS: m/e=226 (M⁺).

c) 2-(3,4-Dihydro-1H-isoquinolin-2-yl)-5,6,7,8-tetrahydro-quinolin-4-yl-amine 1:1 hydrochloride Following the general method described in example 1, the title compound was obtained as an off-white crystalline material by reaction of 2-bromo-5,6,7,8-tetrahydro-quinolin-4-ylamine (example 7b) with 1,2,3,4-tetrahydro-isoquinoline and crystallization of the free base as the hydrochloride salt. Mp. 109–110° C. (MeOH/Et₂O), MS: m/e=279 (M⁺).

EXAMPLE 8

N-[2-(3,4-Dihydro-1H-isoquinolin-2-yl)-6-methyl-pyridin-4-yl]-oxalamic acid ethyl ester With ice bath cooling, a solution of ethyl chlorooxoacetate (2.0 g, 14.6 mmol) in THF (25 ml) was dropwise added to a solution of 2-(3,4-dihydro-1H-isoquinolin-2-yl)-6-methyl-pyridin-4-yl-amine (example 4) (2.9 g, 12.1 mmol) in pyridine (40 ml). The mixture was stirred at 75° C. for 1 hr, evaporated and partitioned (AcOEt/NaHCO₃-solution). The organic phase was dried (Na₂SO₄), concentrated and crystallized yielding 3.1 g (75%) of the title compound as light brown solid. Mp. 128–129° C. (AcOEt), MS: m/e=340 (M+H⁺).

EXAMPLE 9

2-[2-(3,4-Dihydro-1H-isoquinolin-2-yl)-pyridin-4-yl-amino]-ethanol 1:1 hydrochloride a) N-[2-(3,4-Dihydro-1H-isoquinolin-2-yl)-pyridin-4-yl]-oxalamic acid ethyl ester 1:1 hydrochloride Following the general method described in example 8, the title compound was obtained as a white crystalline material by reaction of 2-(3,4-dihydro-1H-isoquinolin-2-yl)-pyridin-4-ylamine (example 1) with ethyl chlorooxoacetate followed by crystallization of the hydrochloride salt. Mp.>187° C. (dec.)(EtOH/Et₂O), MS: m/e=326 (M+H⁺).

b) 2-[2-(3,4-Dihydro-1H-isoquinolin-2-yl)-pyridin-4-yl-amino]-ethanol 1:1 hydrochloride A solution of N-[2-(3,4-dihydro-1 H-isoquinolin-2-yl)-pyridin-4-yl]-oxalamic acid ethyl ester (example 9a) (1.3 g, 4.1 mmol) in THF (41 ml) was cooled in an ice bath and lithium aluminum hydride (0.31 g, 8.2 mmol) was added in 5 portions. The mixture was refluxed for 2 hr, quenched with saturated aqueous Seignette-salt solution and diluted with AcOEt (200 ml). The organic phase was separated, dried (Na$_2$SO$_4$) and concentrated. After chromatography (SiO$_2$ with CH$_2$Cl$_2$/CH$_3$OH/NH$_4$OH=140/10/1) the free base of the title compound was obtained as a colorless oil (0.79 g, 72%). Treatment with hydrogen chloride and triturating with hexane gave the title compound as a white hygroscopic foam. MS: m/e=270 (M+H$^+$).

EXAMPLE 10

2-[2-(3,4-Dihydro-1H-isoquinolin-2-yl)-6-methyl-pyridin-4-yl-amino]-ethanol 1:1 hydrochloride Following the general method described in example 9, N-[2-(3,4-Dihydro-1H-isoquinolin-2-yl)-6-methyl-pyridin-4-yl]-oxalamic acid ethyl ester (example 8) was reacted with lithium aluminum hydride. After workup and chromatography the free base of the title compound was treated with an aliquot of 0.1 N hydrochloric acid, filtered and freeze-dried. MS: m/e=284 (M+H$^+$).

EXAMPLE 11

2-[2-(3,4-Dihydro-1H-isoquinolin-2-yl)-5-methyl-pyridin-4-yl-amino]-ethanol 1:1 fumarate a) N-[2-(3,4-Dihydro-1H-isoquinolin-2-yl)-5-methyl-pyridin-4-yl]-oxalamic acid ethyl ester Following the general method described in example 8, the title compound was obtained as a white crystalline material by reaction of 2-(3,4-dihydro-1H-isoquinolin-2-yl)-5-methyl-pyridin-4-yl-amine (example 3) with ethyl chlorooxoacetate. Mp. 110–111° C. (AcOEt), MS: m/e=340 (M+H$^1$).

b) 2-[2-(3,4-Dihydro-1H-isoquinolin-2-yl)-5-methyl-pyridin-4-yl-amino]-ethanol 1:1 fumarate Following the general method described in example 9, N-[2-(3,4-dihydro-1H-isoquinolin-2-yl)-5-methyl-pyridin-4-yl]-oxalamic acid ethyl ester (example 11a) was reacted with lithium aluminum hydride. After workup and chromatography the free base of the title compound was treated with an aliquot of fumaric acid and crystallized as the white salt. Mp. 232–233° C. (MeOH/Et$_2$O), MS: m/e=284 (M+H$^+$).

EXAMPLE 12

[2-(3,4-Dihydro-1H-isoquinolin-2-yl)-pyridin-4-yl]-methyl-amine 1:1 fumarate a) [2-(3,4-Dihydro-1H-isoquinolin-2-yl)-pyridin-4-yl]-carbamic acid ethyl ester 1:1 hydrochloride In analogy to the general method described in example 8, the title compound was obtained by reaction of 2-(3,4-dihydro-1H-isoquinolin-2-yl)-pyridin-4-yl-amine (example 1) with ethyl chloroformate followed by crystallization of the white hydrochloride salt. Mp.>213° C. (dec) (MeOH/Et$_2$O), MS: m/e=298 (M+H$^+$).

b) [2-(3,4-Dihydro-1H-isoquinolin-2-yl)-pyridin-4-yl]-methyl-amine 1:1 fumarate

Following the general method described in example 9, [2-(3,4-dihydro-1H-isoquinolin-2-yl)-pyridin-4-yl]-carbamic acid ethyl ester (example 12a) was reacted with lithium aluminum hydride. After workup and chromatography the free base of the title compound was treated with an aliquot of fumaric acid to yield a white crystalline material. Mp. 171–172° C. (MeOH/Et$_2$O), MS: m/e=239 (M$^+$).

EXAMPLE 13

[2-(3,4-Dihydro-1H-isoquinolin-2-yl)-pyridin-4-yl]-dimethyl-amine 1:1 fumarate

A solution of 2-(3,4-dihydro-1H-isoquinolin-2-yl)-pyridin-4-y-lamine (example 1) (2.3 g, 10.0 mmol) in formic acid (16 ml) was treated with aqueous formaldehyde solution (8 ml of a 40% solution). The mixture was refluxed for 1 hr followed by evaporation of the volatiles. The residue was partitioned (AcOEt/NaHCO$_3$-solution) and the organic phase was separated, dried (Na$_2$SO$_4$) and concentrated. After chromatography (SiO$_2$ with CH$_2$Cl$_2$/CH$_3$OH/NH$_4$OH=300/10/1) the free base of the title compound was obtained as a colorless oil (1.44 g, 57%). It was crystallized as the white fumarate salt. Mp. 177–178° C. (MeOH/Et$_2$O), MS: m/e=254 (M+H$^+$).

EXAMPLE 14

5-(3,4-Dihydro-1H-isoquinolin-2-yl)-1-methyl-1,4-dihydro-2H-pyrido[4,3-d][1,3]oxazine 1:1 hydrochloride The free base of the title compound was obtained as a minor (less polar) product (0.54 g, 19%) in the synthesis of [2-(3,4-dihydro-1H-isoquinolin-2-yl)-pyridin-4-yl]-dimethyl-amine (example 13). It was crystallized as the white hydrochloride salt. Mp. 220–221° C. (MeOH/Et$_2$O), MS: m/e=282 (M+H$^+$).

EXAMPLE 15

N-[2-(3,4-Dihydro-1H-isoquinolin-2-yl)-pyridin-4-yl]-acetamide 1:1 hydrochloride In analogy to the general method described in example 8, the title compound was obtained by reaction of 2-(3,4-dihydro-1H-isoquinolin-2-yl)-pyridin-4-ylamine (example 1) with acetyl chloride followed by crystallization of the white hydrochloride salt. Mp. 229–230° C. (MeOH/Et$_2$O), MS: m/e=267 (M$^+$).

EXAMPLE 16

[2-(3,4-Dihydro-1H-isoquinolin-2-yl)-pyridin-4-yl]-ethyl-amine 1:1 fumarate

Following the general method described in example 9, N-[2-(3,4-dihydro-1H-isoquinolin-2-yl)-pyridin-4-yl]-acetamide (example 15) was reacted with lithium aluminum hydride. After workup and chromatography the free base of the title compound was treated with an aliquot of fumaric acid and crystallized as the white salt. Mp. 73–74° C. (MeOH/Et$_2$O), MS: m/e=254 (M$^+$).

EXAMPLE 17

Benzyl-[2-(3,4-dihydro-1H-isoquinolin-2-yl)-pyridin-4-yl]-amine a) N-[2-(3,4-Dihydro-1H-isoquinolin-2-yl)-pyridin-4-yl]-benzamide In analogy to the general method described in example 8, the title compound was obtained by reaction of 2-(3,4-dihydro-1H-isoquinolin-2-yl)-pyridin-4-yl-amine (example 1) with benzoyl chloride followed by crystallization of the free base. Mp. 139–140° C. (AcOEt/iPr$_2$O), MS: m/e=330 (M+H$^+$).

b) Benzyl-[2-(3,4-dihydro-1H-isoquinolin-2-yl)-pyridin-4-yl]-amine

Following the general method described in example 9, N-[2-(3,4-dihydro-1H-isoquinolin-2-yl)-pyridin-4-yl]-benzamide (example 17a) was reacted with lithium aluminum hydride. After workup and chromatography the free base of the title compound was treated with hydrogen chloride and triturated with Et$_2$O/pentane. The title compound was obtained as white amorphous material. MS: m/e=315 (M$^+$).

EXAMPLE 18

6-(3,4-Dihydro-1H-isoquinolin-2-yl)-4-methyl-pyridin-2-yl-amine 1:1 hydrochloride Following the general method described in example 1, the title compound was obtained as a white crystalline material by reaction of 6-bromo-4-methyl-pyridin-2-yl-amine (F. Johnson et al., J.Org.Chem., 1962, 27, 2473) with 1,2,3,4- tetrahydro-isoquinoline and crystallization of the free base as the hydrochloride salt. Mp. 196–197° C. (MeOH/Et$_2$O), MS: m/e=240 (M+H$^+$).

EXAMPLE 19
6-(3,4-Dihydro-1H-isoquinolin-2-yl)-pyridin-2-yl-amine 1:1 hydrochloride Following the general method described in example 1, the title compound was obtained as a light brown crystalline material by reaction of 6-bromo-pyridin-2-yl-amine with 1,2,3,4-tetrahydro-isoquinoline and crystallization of the free base as the hydrochloride salt. Mp. 177–178° C. (MeOH/Et$_2$O), MS: m/e=225 (M$^+$).

EXAMPLE 20
2-(4-Methyl-pyridin-2-yl)-1,2,3,4-tetrahydro-isoquinoline 1:1 hydrochloride Following the general method described in example 1, the title compound was obtained as a white crystalline material by reaction of 2-bromo-4-methyl-pyridine with 1,2,3,4-tetrahydro-isoquinoline and crystallization of the free base as the hydrochloride salt. Mp. 142–143° C. (MeOH/Et$_2$O), MS: m/e=: 224 (M$^+$).

EXAMPLE 21
2-(3,4-Dihydro-1H-isoquinolin-2-yl)-pyridin-3-yl-amine 1:1 hydrochoride a) 2-(3-Nitro-pyridin-2-yl)-1,2,3,4-tetrahydro-isoquinoline A suspension of 2-chloro-5-nitro-pyridine (1.58 g, 10 mmol) in isopropanol (30 ml) was treated at rt with 1,2,3,4-tetrahydro-isoquinoline (2.6 g, 20 mmol). The resulting mixture was stirred for 3 hr. The precipitate was filtered, partitioned (AcOEt/H$_2$O) and the organic phase dried (Na$_2$SO$_4$). After evaporation of the solvent the title compound was obtained as a yellow solid mass (1.4 g, 55%), MS: m/e=256 (M+H$^+$).

b)-(3,4-Dihydro-1H-isoquinolin-2-yl)-pyridin-3-yl-amine 1:1 hydrochoride

To a solution of 2-(3-nitro-pyridin-2-yl)-1,2,3,4-tetrahydro-isoquinoline (example 21a) (1.4 g, 5.5 mmol) in methanol (50 ml) palladium on carbon (10%, 140 mg) was added and the resulting mixture was hydrogenated for 24 hr. After filtration of the catalyst, the reaction mixture was concentrated and chromatographed (SiO$_2$ with hexane/AcOEt=4/1) to yield the free base of the title compound (0.64 g, 52%) as a brown oil. Treatment with hydrogen chloride gave white crystals. Mp. 195–196° C. (MeOH/Et$_2$O), MS: m/e=225 (M$^+$).

EXAMPLE 22
C-[6-(3,4-Dihydro-1H-isoquinolin-2-yl)-pyridin-2-yl]-methylamine hydrochloride (1:2)

a) 6-(3,4-Dihydro-1H-isoquinolin-2-yl)-pyridine-2-carboxylic acid amide

Following the general method described in example 1, the title compound was obtained as a light yellow crystalline material by reaction of 6-chloro-pyridine-2-carboxylic acid amide with 1,2,3,4-tetrahydro-isoquinoline and crystallization of the free base. Mp. 145–150° C. (AcOEt/hexane), MS: m/e=253 (M$^+$).

b) C-[6-(3,4-Dihydro-1H-isoquinolin-2-yl)-pyridin-2-yl]-methylamine hydrochloride (1:2)

Following the general method described in example 9, 6-(3,4-dihydro-1H-isoquinolin-2-yl)-pyridine-2-carboxylic acid amide (example 22a) was reacted with lithium aluminum hydride. After workup and chromatography the free base of the title compound was treated with hydrogen chloride and crystallized as the off white salt. Mp. 192–195° C. (iPr$_2$O), MS: m/e=239 (M$^+$).

EXAMPLE 23
5-(3,4-Dihydro-1H-isoquinolin-2-yl)-1-ethyl-1,4-dihydro-2H-pyrido[4,3-d][1,3]hydrochloride A solution of [2-(3,4-dihydro-1H-isoquinolin-2-yl)-pyridin-4-yl]-ethyl-amine (example 16) (0.8 g, 3.1 mmol) in formic acid (16 ml) was treated with aqueous formaldehyde solution (8 ml of a 40% solution). The mixture was refluxed for 1 hr followed by evaporation of the volatiles. The residue was partitioned (AcOEt/NaHCO$_3$-solution) and the organic phase was separated, dried (Na$_2$SO$_4$) and concentrated. After chromatography (SiO$_2$ with CH$_2$Cl/CH$_3$OH/NH$_4$OH= 400/10/1) the free base of the title compound was obtained as a colorless oil (0.74 g, 81%). It was crystallized as the white hydrochloride salt. Mp. 197–198° C. (MeOH/Et$_2$O), MS: m/e=295 (M$^+$).

EXAMPLE 24
2-Pyridin-4-yl-1,2,3,4-tetrahydro-isoquinoline

A mixture of 4-chloro-pyridine 1:1 hydrochloride (24.5 g, 163 mmol) and 1,2,3,4-tetrahydro-isoquinoline (65.3 g, 490 mmol) was slowly heated to 150° C. After 30 min the reaction mixture was cooled to rt, H$_2$O (700 ml) and 2N NaOH (82 ml) was added followed by extraction with AcOEt (5 times 300 ml). The combined organic phases were dried (Na$_2$SO$_4$), and the solvent was evaporated. After trituration with pentane and recrystallization the title compound (30.2 g, 88%) was obtained as a light brown crystalline material. Mp. 95–96° C. (AcOEt), MS: m/e=210 (M$^+$).

EXAMPLE 25
5-Chloro-2-pyridin-4-yl-1,2,3,4-tetrahydro-isoquinoline 1:1 hydrochloride A mixture of 4-bromo-pyridine 1:1 hydrochloride (0.95 g, 4.9 mmol), 5-chloro-1,2,3,4-tetrahydro-isoquinoline (C. Kaiser et al., J. Med. Chem., 1980, 23, 506) (0.99 g, 4.9 mmol) and Na$_2$CO$_3$ (1.8 g, 17 mmol) in N-methyl-pyrrolidinone (15 ml) was stirred at 170° C. for 3.5 hr. All volatiles were evaporated (at 50° C., 0.01 mbar) and the residue was partitioned (AcOEt/H$_2$O). The organic phase was dried (Na$_2$SO$_4$), concentrated and chromatographed (SiO$_2$ with CH$_2$Cl$_2$/CH$_3$OH/NH$_4$OH=250/10/1). The free base of the title compound was obtained as a light brown crystalline material (0.71 g, 59%). It was crystallized as the white hydrochloride salt. Mp. 258–259° C. (MeOH/Et$_2$O), MS: m/e=244 (M$^+$).

EXAMPLE 26
8-Chloro-2-pyridin-4-yl-1,2,3,4-tetrahydro-isoquinoline 1:1 fumarate Following the general method described in example 25, the free base of the title compound was obtained by reaction of 4-bromo-pyridine 1:1 hydrochloride with 8-chloro-1,2,3,4-tetrahydro-isoquinoline (C. Kaiser et al., J.Med.Chem., 1980, 23, 506) and Na$_2$CO$_3$ in N-methyl-pyrrolidinone. It was crystallized as the light yellow fumarate salt. Mp. 178–179° C. (MeOH), MS: m/e=244 (M$^+$).

EXAMPLE 27
6-Chloro-2-pyridin-4-yl-1,2,3,4-tetrahydro-isoquinoline 1:1 hydrochlorid Following the general method described in example 25, the free base of the title compound was obtained by reaction of 4-bromo-pyridine 1:1 hydrochloride with 6-chloro-1,2,3,4-tetrahydro-isoquinoline (C. Kaiser et al., J.Med.Chem., 1980, 23, 506) and Na$_2$CO$_3$ in N-methyl-pyrrolidinone. It was crystallized as the light brown hydrochloride salt. Mp.>250° C. (MeOH/Et$_2$O), MS: m/e=245 (M+H$^+$).

EXAMPLE 28

7-Chloro-2-pyridin-4-yl-1,2,3,4-tetrahydro-isoquinoline

In analogy to the general method described in example 25, the title compound was obtained as a white crystalline material by reaction of 4-chloro-pyridine 1:1 hydrochloride with 7-chloro-1,2,3,4-tetrahydro-isoquinoline (C. Kaiser et al., J.Med.Chem., 1980, 23, 506) and $Cs_2CO_3$ in DMF. Mp. 100–101° C. (AcOEt/pentane), MS: m/e=244 ($M^+$).

EXAMPLE 29 rac.-4-Methyl-2-pyridin-4-yl-1,2,3,4-tetrahydro-isoquinoline 1:1 hydrochloride

Following the general method described in example 25, the free base of the title compound was obtained by reaction of 4-bromo-pyridine 1:1 hydrochloride with rac.-1-methyl-1,2,3,4-tetrahydro-isoquinoline (G. Grunewald et al., J. Med. Chem., 1988, 31, 433) and $Na_2CO_3$ in N-methyl-pyrrolidinone. It was crystallized as the off-white hydrochloride salt. Mp. 224–227° C. (MeOH/$Et_2O$), MS: m/e=224 ($M^+$).

EXAMPLE 30

4-(3,4-Dihydro-1H-isoquinolin-2-yl)-pyridin-2-yl-amine

Following the general method described in example 24, 4-bromo-pyridin-2-yl-amine (H. J. den Hertog, Recl.Trav.Chim.Pays-Bas, 1945, 64, 85) was reacted with 1,2,3,4-tetrahydro-isoquinoline. The crude product was chromatographed ($SiO_2$ with $CH_2Cl_2/CH_3OH/NH_4OH$=200/10/1) and crystallized to yield the title compound as an off-white crystalline material. Mp. 160–161° C. ($CH_3CN$), MS: m/e=226 ($M+H^+$).

EXAMPLE 31

2-(2-Methyl-pyridin-4-yl)-1,2,3,4-tetrahydro-isoquinoline 1:1 fumarate

Following the general method described in example 24, 4-bromo-2-methyl-pyridine (S. Ochiai, Pharm.Bull., 1954, 2, 147) was reacted with 1,2,3,4-tetrahydro-isoquinoline. The crude product was chromatographed ($SiO_2$ with $CH_2Cl_2/CH_3OH/NH_4OH$=200/10/1) and crystallized as the white fumarate salt. Mp. 155–156° C. (MeOH/$Et_2O$), MS: m/e=225 ($M+H^+$).

EXAMPLE 32

4-(3,4-Dihydro-1H-isoquinolin-2-yl)-6-methyl-pyridin-2-yl-amine 1:1 fumarate a) 4-Bromo-6-methyl-pyridin-2-yl-amine A mixture of 2,4-dibromo-6-methyl-pyridine (J. Bernstein et al., J. Amer. Chem. Soc., 1947, 69, 1147) (22.6 g, 90 mmol) and aqueous ammonia (25%, 260 ml) was stirred in an autoclave at 160° C. for 4 hr. The reaction mixture was cooled to rt and extracted with $Et_2O$. The organic phase was dried ($Na_2SO_4$), concentrated and chromatographed ($SiO_2$ with AcOEt/hexane/$NEt_3$=10/30/1) to yield the title compound as a white crystalline material (4.0 g, 6%). NMR (250 MHz, DMSO): δ=3.33 (s, 3H, C$\underline{H}_3$), 6.13 (s, broad, 2H, N$\underline{H}_2$), 6.44 (s, 1H, arom-$\underline{H}$), 6.54 (s, 1H, arom-$\underline{H}$).

b) 4-(3,4-Dihydro-1H-isoquinolin-2-yl)-6-methyl-pyridin-2-yl-amine 1:1 fumarate

Following the general method described in example 24, 4-bromo-6-methyl-pyridin-2-yl-amine (example 32a) was reacted with 1,2,3,4-tetrahydro-isoquinoline. The crude product was chromatographed ($SiO_2$ with $CH_2Cl_2/CH_3$OH/$NH_4OH$=200/10/1) and crystallized as the white fumarate salt. Mp.>270° C. (MeOH), MS: m/e=240 ($M+H^+$).

EXAMPLE 33

N-[4-(3,4-Dihydro-1H-isoquinolin-2-yl)-6-methyl-pyridin-2-yl]-oxalamic acid ethyl ester 1:1 hydrochloride Following the general method described in example 8, the title compound was obtained as a light yellow crystalline material by reaction of 4-(3,4-dihydro-1H-isoquinolin-2-yl)-6-methyl-pyridin-2-yl-amine (example 32) with ethyl chlorooxoacetate followed by crystallization of the hydrochloride salt. Mp.>160° C. (dec.)(EtOH/$Et_2O$), MS: m/e=340 ($M+H^+$).

EXAMPLE 34

N-[4-(3,4-Dihydro-1H-isoquinolin-2-yl)-6-methyl-pyridin-2-yl]-2-hydroxy-acetamide A solution of N-[4-(3,4-dihydro-1H-isoquinolin-2-yl)-6-methyl-pyridin-2-yl]-oxalamic acid ethyl ester (example 33) (0.43 g, 1.3 mmol) in THF (20 ml) was cooled in an ice bath and lithium aluminum hydride (0.12 g, 3.2 mmol) was added in. The mixture was stirred at rt for 2 hr, quenched with saturated aqueous Seignette-salt solution and filtered. The organic phase was dried ($Na_2SO_4$) and concentrated. After chromatograpy ($SiO_2$ with $CH_2Cl/CH_3OH/NH_4OH$=200/10/1) the title compound was obtained as a colorless oil (0.18 g, 47%). Mp. 160–162° C. (AcOEt), MS: m/e=296 ($M-H^-$).

EXAMPLE 35

2-[4-(3,4-Dihydro-1H-isoquinolin-2-yl)-6-methyl-pyridin-2-yl-amino]-ethanol 1:1 fumarate Following the general method described in example 9, N-[4-(3,4-dihydro-1H-isoquinolin-2-yl)-6-methyl-pyridin-2-yl]-oxalamic acid ethyl ester (example 33) was reacted with lithium aluminum hydride. After workup and chromatography the free base of the title compound was treated with an aliquot of fumaric acid and crystallized as the white salt. Mp. 160° C. (MeOH), MS: m/e=284 ($M+H^+$).

EXAMPLE A

Tablet Formulation (Wet Granulation)

| | | mg/tablet | | |
|---|---|---|---|---|
| Item | Ingredients | 5 mg | 25 mg | 100 mg | 500 mg |
| 1. | Active Ingredient* | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

*(Compound of formula 1A, IB, combinations thereof or a pharmaceutically acceptable salt thereof)

Manufacturing Procedure

1. Mix items 1, 2, 3 and 4 and granulate with purified water.
2. Dry the granulation at 50° C.
3. Pass the granulation through suitable milling equipment.
4. Add item 5 and mix for three minutes; compress on a suitable press.

EXAMPLE B

Capsule Formulation

| Item | Ingredients | 5 mg | 25 mg | 100 mg | 500 mg |
|---|---|---|---|---|---|
| 1. | Active Ingredient | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2, and 3 in a suitable mixer for 30 minutes.
2. Add items 4 and 5 and mix for 3 minutes.
3. Fill into a suitable capsule.
4. Add item 5 and mix for three minutes; compress on a suitable press.

What is claimed is:
1. A compound of formula:

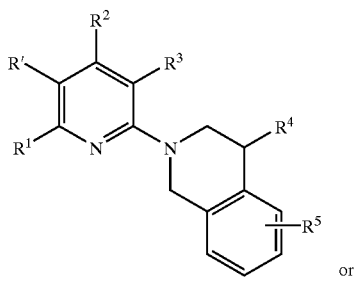

IA or

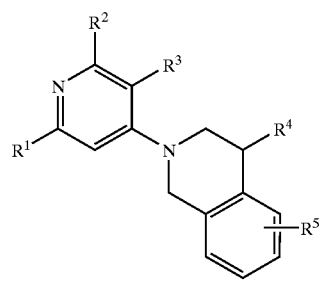

IB wherein
   $R^1$ is selected from the group consisting of hydrogen, lower alkyl, $-(CH_2)_n OH$, $-(CH_2)_n-N(R^6)_2$, $-NR^6-C(O)C(O)O$-lower alkyl, $-NR^6-(CH_2)_n-$ OH, $-NR^6C(O)$-lower alkyl, $-NH$-benzyl or $NR^6C(O)-(CH_2)_n-OH$;
   $R^2$ is selected from the group consisting of $-(CH_2)_n-$ OH, $-(CH_2)_n-N(R^6)_2$, $-NR^6C(O)C(O)O$-lower alkyl, $-NR^6-(CH_2)_n-OH$, $-NR^6C(O)$-lower alkyl, $-NH$-benzyl or $NR^6C(O)-(CH_2)_n-OH$;
   $R^6$ is independently from each other hydrogen or lower alkyl;
   R' is hydrogen or lower alkyl;
   $R^3$ is hydrogen or amino;
   $R^4$ is hydrogen or lower alkyl;
   $R^5$ is hydrogen or halogen; or
   $R^2$ and $R^3$ together with the carbon atoms to which they are attached form the group $-N(R^6)-CH_2-O-CH_2-$; and
   n is 0, 1, 2 or 3;
   or a pharmaceutically acceptable acid addition salt thereof, provided that the compound is not 2-(5-methyl-pyridin-2-yl)-1,2,3,4-tetrahydro-isoquinoline or 4-(3,4-dihydro-1H-isoquinolin-2yl)-pyridin-3-ylamine.

2. A compound of formula:

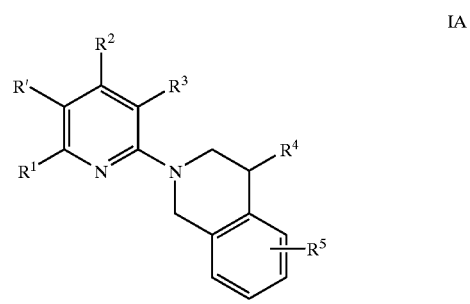

IA wherein
   $R^1$ is selected from the group consisting of hydrogen, lower alkyl, $-(CH_2)_n-OH$, $-(CH_2)_n-N(R^6)_2$, $-NR^6C(O)C(O)O$-lower alkyl, $-NR^6-(CH_2)_n-$ OH, $-NR^6C(O)$-lower alkyl, $-NH$-benzyl or $NR^6C(O)-(CH_2)_n-OH$;
   $R^2$ is selected from the group consisting of $-(CH_2)_n-$ OH, $-(CH_2)_n-N(R^6)_2$, $-NR^6C(O)C(O)Q$-lower alkyl, $-NR^6-(CH_2)_n-OH$, $-NR^6C(O)$-lower alkyl, $-NH$-benzyl or $NR^6C(O)-(CH_2)_n-OH$;
   $R^6$ is independently selected from hydrogen or lower alkyl;
   R' is hydrogen or lower alkyl;
   $R^3$ is hydrogen or amino;
   $R^4$ is hydrogen or lower alkyl;
   $R^5$ is hydrogen or halogen; or
   $R^2$ and $R^3$ together with the carbon atoms to which they are attached form the group $-N(R^6)-CH_2-O-CH_2-$; and
   n is 0, 1, 2 or 3;
   or a pharmaceutically acceptable acid addition salt thereof, provided that the compound is not 2-(5-methyl-pyridin-2-yl)-1,2,3,4-tetrahydro-isoquinoline.

3. A compound of formula IA in accordance with claim 2, wherein $R^2$ is amino.

4. A compounds of formula IA in accordance with claim 3, selected from the group consisting of
   2-(3,4-dihydro-1H-isoquinolin-2-yl)-pyridin-4-yl-amine,
   Rac-2-(4-methyl-3,4-dihydro-1H-isoquinolin-2-yl)-pyridin-4-yl-amine,
   2-(3,4-dihydro-1H-isoquinolin-2-yl)-5-methyl-pyridin-4-yl-amine,
   2-(3,4-dihydro-1H-isoquinolin-2-yl)-6-methyl-pyridin-4-yl-amine,
   2-(3,4-dihydro-1H-isoquinolin-2-yl)-6-ethyl-pyridin-4-yl-amine and
   [4-amino-6-(3,4-dihydro-1H-isoquinolin-2-yl)-pyridin-2-yl]-methanol.

5. A compound of formula IA in accordance with claim 2, wherein $R^2$ is $-NH(CH_2)_2OH$.

6. A compound of formula IA in accordance with claim 5, selected from the group consisting of
   2-[2-(3,4-dihydro-1H-isoquinolin-2-yl)-pyridin-4-yl-amino]-ethanol, 2-[2-(3,4-dihydro-1H-isoquinolin-2-yl)-6-methyl-pyridin-4-yl-amino]-ethanol and 2-[2-(3,4-dihydro-1H-isoquinolin-2-yl)-5-methyl-pyridin-4-yl-amino]-ethanol.

7. A compound of formula IA in accordance with claim 2, wherein R² is —NH-lower alkyl.

8. A compound of formula IA in accordance with claim 7, selected from the group consisting of

[2-(3,4-dihydro-1H-isoquinolin-2-yl)-pyridin-4-yl]-methyl-amine and

[2-(3,4-dihydro-1H-isoquinolin-2-yl)-pyridin-4-yl]-dimethyl-amine.

9. A compound of formula:

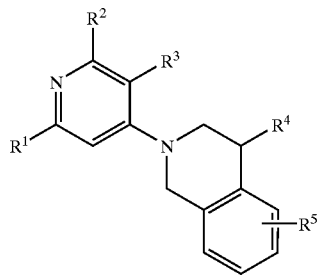

IB wherein

R¹ is selected from the group consisting of hydrogen, lower alkyl, —(CH₂)ₙ—OH, —(CH₂)ₙ—N(R⁶)₂, —NR⁶C(O)C(O)O-lower alkyl, —NR⁶—(CH₂)ₙ—OH, —NR⁶C(O)-lower alkyl, —NH-benzyl or NR⁶C(O)—(CH₂)ₙ—OH;

R² is selected from the group consisting of —(CH₂)ₙ—OH, —(CH₂)ₙ—N(R⁶)₂, —NR⁶C(O)C(O)O-lower alkyl, —NR⁶—(CH₂)ₙ—OH, —NR⁶C(O)-lower alkyl, —NH-benzyl or NR⁶C(O)—(CH₂)ₙ—OH;

R⁶ is independently selected from hydrogen or lower alkyl

R' is hydrogen or lower alkyl;

R³ is hydrogen or amino;

R⁴ is hydrogen or lower alkyl;

R⁵ is hydrogen or halogen; or

R¹ and R' together with the carbon atoms to which they are attached form the group —(CH₂)₄—; or R² and R³ together with the carbon atoms to which they are attached form the group —N(R⁶)—CH₂—O—CH₂—; and n is 0, 1, 2 or 3;

or a pharmaceutically acceptable acid addition salt thereof, provided that the compound is not 4-(3,4-dihydro-1H-isoquinolin-2-yl)-pyridin-3-ylamine.

10. A compound of formula IB according to claim 9, wherein R² is hydrogen.

11. A compound of formula IB according to claim 10, selected from the group consisting of 2-pyridin-4-yl-1,2,3,4-tetrahydro-isoquinoline and 2-(2-methyl-pyridin-4-yl)-1,2,3,4-tetrahydro-isoquinoline.

12. A compound of formula IB according to claim 9, wherein R² is amino.

13. A compound of formula IB according to claim 12, selected from the group consisting of 4-(3,4-dihydro-1H-isoquinolin-2-yl)-pyridin-2-yl-amine and 4-(3,4-dihydro-1H-isoquinolin-2-yl)-6-methyl-pyridin-2-yl-amine.

14. A compound of formula ID according to claim 9, wherein R² is selected from the group consisting of —NHC(O)C(O)OCH₂CH₃ and —NH(CH₂)₂OH.

15. A compound of formula IB according to claim 14, selected from the group consisting of:

N-[4-(3,4-dihydro-1H-isoquinolin-2-yl)-6-methyl-pyridin-2-yl]-oxalamic acid ethyl ester and 2-[4-(3,4-dihydro-1H-isoquinolin-2-yl)-6-methyl-pyridin-2-yl-amino]-ethanol.

16. A pharmaceutical composition comprising a compound of formula IA, a compound of formula IB, or a compound of formula IA and a compound of formula IB, according to claim 1, or a pharmaceutically acceptable salt thereof and a pharmaceutically acceptable carrier.

17. A compound of formula:

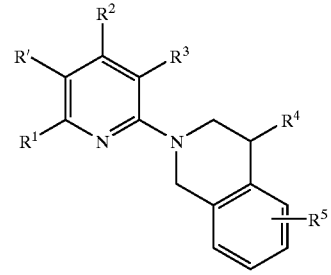

IA or

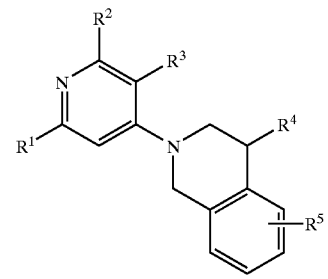

IB wherein

R¹ is selected from the group consisting of —(CH₂)ₙ—OH, —(CH₂)ₙ—N(R⁶)₂, —NR⁶C(O)C(O)O-lower alkyl, —NR⁶—(CH₂)ₙ—OH,—NR⁶C(O)-lower alkyl, —NH-benzyl or NR⁶C(O)—(CH₂)ₙ—OH;

R² is selected from the group consisting of hydrogen, lower alkyl, —(CH₂)ₙ—OH, —(CH₂)ₙ—N(R⁶)₂, —NR⁶C(O)C(O)O-lower alkyl, —NR⁶—(CH₂)ₙ—OH,—NR⁶C(O)-lower alkyl, —NH-benzyl or NR⁶C(O)—(CH₂)ₙ—OH;

R⁶ is independently from each other hydrogen or lower alkyl;

R' is hydrogen or lower alkyl;

R³ is hydrogen or amino;

R⁴ is hydrogen or lower alkyl;

R⁵ is hydrogen or halogen; or

R² and R³ together with the carbon atoms to which they are attached form the group —N(R⁶)—CH₂—O—CH₂—; and n is 0, 1, 2 or 3;

or a pharmaceutically acceptable acid addition salt thereof, provided that the compound is not 2-(5-methyl-pyridin-2-yl)-1,2,3,4-tetrahydro-isoquinoline or 4-(3,4-dihydro-1H-isoquinolin-2-yl)-pyridin-3-ylamine.

18. A compound of formula:

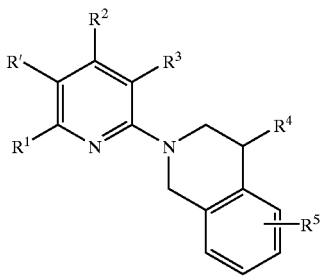

IA wherein
R¹ is selected from the group consisting of —(CH₂)ₙ—OH, —(CH₂)ₙ—N(R⁶)₂, —NR⁶C(O)C(O)O-lower alkyl, —NR⁶—(CH₂)ₙ—OH,—NR⁶C(O)-lower alkyl, —NH-benzyl or NR⁶C(O)—(CH₂)ₙ—OH;

R² selected from the group consisting of hydrogen, lower alkyl, —(CH₂)ₙ—OH, —(CH₂)ₙ—N(R⁶)₂, —NR⁶C(O)C(O)O-lower alkyl, —NR⁶—(CH₂)ₙ—OH,—NR⁶C(O)-lower alkyl, —NH-benzyl or NR⁶C(O)—(CH₂)ₙ—OH;

R⁶ is independently selected from hydrogen or lower alkyl;

R' is hydrogen or lower alkyl;

R³ is hydrogen or amino;

R⁴ is hydrogen or lower alkyl;

R⁵ is hydrogen or halogen; or

R² and R³ together with the carbon atoms to which they are attached form the group —N(R⁶)—CH₂—O—CH₂—; and n is 0, 1, 2 or 3;

or a pharmaceutically acceptable acid addition salt thereof, provided that the compound is not 2-(5-methyl-pyridin-2-yl)-1,2,3,4-tetrahydro-isoquinoline.

19. A compound of formula:

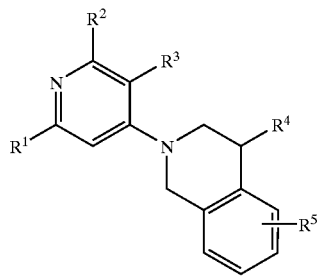

IB wherein
R¹ is selected from the group consisting of —(CH₂)ₙ—OH, —(CH₂)ₙ—N(R⁶)₂, —NR⁶C(O)C(O)O-lower alkyl, —NR⁶—(CH₂)ₙ—OH,—NR⁶C(O)-lower alkyl, —NH-benzyl or NR⁶C(O)—(CH₂)ₙ—OH;

R² is selected from the group consisting of hydrogen, lower alkyl, —(CH₂)ₙ—OH, —(CH₂)ₙ—N(R⁶)₂, —NR⁶C(O)C(O)O-lower alkyl, —NR⁶—(CH₂)ₙ—OH,—NR⁶C(O)-lower alkyl, —NH-benzyl or NR⁶C(O)—(CH₂)ₙ—OH;

R⁶ is independently selected from hydrogen or lower alkyl

R' is hydrogen or lower alkyl;

R³ is hydrogen or amino;

R⁴ is hydrogen or lower alkyl;

R⁵ is hydrogen or halogen; or

R² and R³ together with the carbon atoms to which they are attached form the group —N(R⁶)—CH₂—O—CH₂—; and n is 0, 1, 2 or 3;

or a pharmaceutically acceptable acid addition salt thereof, provided that the compound is not 4-(3,4-dihydro-1H-isoquinolin-2-yl)-pyridin-3-ylamine.

20. A pharmaceutical composition comprising a compound of formula IA, a compound of formula IB, or a compound of formula IA and a compound of formula IB, according to claim 17, or a pharmaceutically acceptable salt thereof and a pharmaceutically acceptable carrier.

21. A compound of formula:

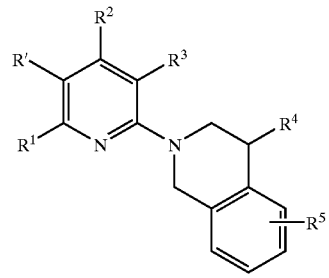

IA or

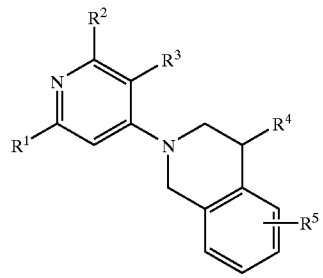

IB wherein
R¹ and R² are independently selected from the group consisting of hydrogen, lower alkyl, —(CH₂)ₙ—OH, —(CH₂)ₙ—N(R⁶)₂, —NR⁶C(O)C(O)O-lower alkyl, —NR⁶—(CH₂)ₙ—OH,—NR⁶C(O)-lower alkyl, —NH-benzyl or NR⁶C(O)—(CH₂)ₙ—OH;

R⁶ is independently from each other hydrogen or lower alkyl;

R' is hydrogen or lower alkyl;

R³ is hydrogen or amino;

R⁴ is hydrogen or lower alkyl;

R⁵ is hydrogen or halogen; or

R² and R³ together with the carbon atoms to which they are attached form the group —N(R⁶)—CH₂—O—CH₂—; and n is 0, 1, 2 or 3;

or a pharmaceutically acceptable acid addition salt thereof, provided that the compound is not 2-(5-methyl-pyridin-2-yl)-1,2,3,4-tetrahydro-isoquinoline or 4-(3,4-dihydro-1H-isoquinolin-2-yl)-pyridin-3-ylamine and provided that R¹, R', R², R³, R⁴, and R⁵ are not all hydrogen.

22. A compound of formula:

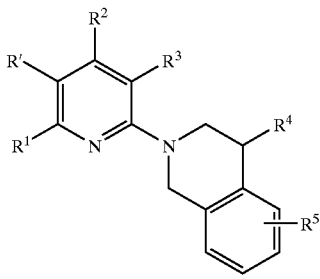

IA wherein

- $R^1$ and $R^2$ are independently selected from the group consisting of hydrogen, lower alkyl, —$(CH_2)_n$—OH, —$(CH_2)_n$—$N(R^6)_2$, —$NR^6C(O)C(O)O$-lower alkyl, —$NR^6$—$(CH_2)_n$—OH, —$NR^6C(O)$-lower alkyl, —NH-benzyl or $NR^6C(O)$—$(CH_2)_n$—OH;
- $R^6$ is independently selected from hydrogen or lower alkyl;
- R' is hydrogen or lower alkyl;
- $R^3$ is hydrogen or amino;
- $R^4$ is hydrogen or lower alkyl;
- $R^5$ is hydrogen or halogen; or
- $R^2$ and $R^3$ together with the carbon atoms to which they are attached form the group —$N(R^6)$—$CH_2$—O—$CH_2$—; and
- n is 0, 1, 2 or 3;

or a pharmaceutically acceptable acid addition salt thereof, provided that the compound is not 2-(5-methyl-pyridin-2-yl)-1,2,3,4-tetrahydro-isoquinoline or 4-(3,4-dihydro-1H-isoquinolin-2-yl)-pyridin-3-ylamine and provided that $R^1$, R', $R^2$, $R^3$, $R^4$, and $R^5$ are not all hydrogen.

23. A compound of formula:

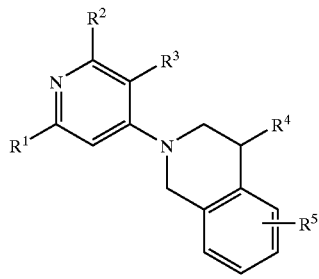

IB wherein

- $R^1$ and $R^2$ are independently selected from the group consisting of hydrogen, lower alkyl, —$(CH_2)_n$—OH, —$(CH_2)_n$—$N(R^6)_2$, —$NR^6C(O)C(O)O$-lower alkyl, —$NR^6$—$(CH_2)_n$—OH, —$NR^6C(O)$-lower alkyl, —NH-benzyl or $NR^6C(O)$—$(CH_2)_n$—OH;
- $R^6$ is independently selected from hydrogen or lower alkyl
- R' is hydrogen or lower alkyl;
- $R^3$ is hydrogen or amino;
- $R^4$ is hydrogen or lower alkyl;
- $R^5$ is hydrogen or halogen; or
- $R^1$ and R' together with the carbon atoms to which they are attached form the group —$(CH_2)_4$—; or
- $R^2$ and $R^3$ together with the carbon atoms to which they are attached form the group —$N(R^6)$—$CH_2$—O—$CH_2$—; and
- n is 0, 1, 2 or 3;

or a pharmaceutically acceptable acid addition salt thereof, provided that the compound is not 4-(3,4-dihydro-1H-isoquinolin-2-yl)-pyridin-3-ylamine and provided that $R^1$, R', $R^2$, $R^3$, $R^4$, and $R^5$ are not all hydrogen.

* * * * *

UNITED STATES PATENT AND TRADEMARK OFFICE
CERTIFICATE OF CORRECTION

PATENT NO. : 6,831,087 B2
DATED : December 14, 2004
INVENTOR(S) : Alexander Alanine et al.

It is certified that error appears in the above-identified patent and that said Letters Patent is hereby corrected as shown below:

Column 34,
Line 29, -NR$^6$C(O)C(O)Q-lower" should read -- NR$^6$C(O)C(O)O-lower --.
Line 48, "A compounds" should read -- A compound --.

Column 36,
Line 3, "formula ID" should read -- formula IB --.

Column 38,
Line 65, "4-(3.4-dihydro-1H-isoquinolin-2-yl)" should read
-- 4-(3,4-dihydro-1H-isoquinolin-2-yl) --.

Signed and Sealed this

Twenty-fourth Day of May, 2005

JON W. DUDAS
*Director of the United States Patent and Trademark Office*